(12) United States Patent
Sonnenschein et al.

(10) Patent No.: US 8,128,645 B2
(45) Date of Patent: *Mar. 6, 2012

(54) STAPLER FOR ENDOSCOPES

(75) Inventors: Elazar Sonnenschein, Omer (IL);
Minelu Sonnenschein, Meitar (IL);
Lawrence Crainich, Charlestown, NH (US)

(73) Assignee: Medigus Ltd., Beer-Sheva (IL)

( * ) Notice: Subject to any disclaimer, the term of this patent is extended or adjusted under 35 U.S.C. 154(b) by 1607 days.

This patent is subject to a terminal disclaimer.

(21) Appl. No.: 11/062,077

(22) Filed: Feb. 18, 2005

(65) Prior Publication Data

US 2005/0145674 A1 Jul. 7, 2005

Related U.S. Application Data

(63) Continuation of application No. 10/030,018, filed as application No. PCT/IL01/00719 on Aug. 2, 2001, now Pat. No. 6,872,214.

(30) Foreign Application Priority Data

Nov. 20, 2000 (IL) .......................... 139788

(51) Int. Cl.
*A61B 17/08* (2006.01)
*A61B 17/04* (2006.01)
*A61B 1/00* (2006.01)
(52) U.S. Cl. ...................... 606/153; 227/176.1; 600/104
(58) Field of Classification Search .................. 606/139, 606/153, 142; 227/176.1; 600/117, 106, 600/104; 128/898
See application file for complete search history.

(56) References Cited

U.S. PATENT DOCUMENTS

| | | | |
|---|---|---|---|
| 4,304,236 A | 12/1981 | Conta et al. | |
| 4,612,933 A | 9/1986 | Brinkerhoff et al. | |
| 4,637,767 A | 1/1987 | Yaotani et al. | |
| 4,848,637 A | 7/1989 | Pruitt | |
| 5,129,570 A | 7/1992 | Schulze et al. | |
| 5,197,649 A | 3/1993 | Bessler et al. | |
| 5,271,543 A | 12/1993 | Grant et al. | |
| 5,312,024 A | 5/1994 | Grant et al. | |
| 5,382,231 A | 1/1995 | Shlain | |
| 5,395,030 A | 3/1995 | Kuramoto et al. | |
| 5,403,326 A | 4/1995 | Harrison et al. | |
| 5,411,508 A | 5/1995 | Bessler et al. | |
| 5,441,507 A | 8/1995 | Wilk | |
| 5,452,836 A | 9/1995 | Huitema et al. | |

(Continued)

FOREIGN PATENT DOCUMENTS

WO   WO 00/53102   9/2000

(Continued)

*Primary Examiner* — Tuan Nguyen
(74) *Attorney, Agent, or Firm* — Roach Brown McCarthy & Gruber, P.C.; Kevin D. McCarthy

(57) ABSTRACT

A stapling device for a surgical endoscopic device provided with at least one flexible portion, comprising a staple-firing portion and an anvil portion, wherein one of the staple firing portions and one of the anvil portions are located longitudinally displaced from one another along the longitudinal axis of the endoscopic device, with at least a part of said flexible portion between them. The parts of the stapling device are in correct working relationship when one or more alignment and/or locking pins or screws that are stored in one of the staple firing portions or one of the anvil portions are extended and engage and lock or screw into receptacles that have been provided on the other of the staple firing portion or of the anvil portion.

11 Claims, 26 Drawing Sheets

U.S. PATENT DOCUMENTS

| | | | |
|---|---|---|---|
| 5,465,895 A | 11/1995 | Knodel et al. | |
| 5,571,116 A | 11/1996 | Bolanos et al. | |
| 5,603,443 A | 2/1997 | Clark et al. | |
| 5,609,285 A | 3/1997 | Grant et al. | |
| 5,630,540 A | 5/1997 | Blewett | |
| 5,630,541 A | 5/1997 | Williamson, IV et al. | |
| 5,676,674 A | 10/1997 | Bolanos et al. | |
| 5,727,553 A | 3/1998 | Saad | |
| 5,772,099 A | 6/1998 | Gravener | |
| 5,772,673 A | 6/1998 | Cuny et al. | |
| 5,779,130 A | 7/1998 | Alesi et al. | |
| 5,787,897 A | 8/1998 | Kieturakis | |
| 5,814,055 A | 9/1998 | Knodel et al. | |
| 5,833,616 A | 11/1998 | Gruner et al. | |
| 5,833,696 A | 11/1998 | Whitfield et al. | |
| 5,879,115 A | 3/1999 | Medal | |
| 6,050,472 A | 4/2000 | Shibata | |
| 6,099,542 A | 8/2000 | Cohn et al. | |
| 6,159,146 A * | 12/2000 | El Gazayerli | 600/106 |
| 6,338,737 B1 | 1/2002 | Toledano | |
| 6,506,196 B1 * | 1/2003 | Laufer | 606/142 |
| 6,592,596 B1 * | 7/2003 | Geitz | 606/139 |
| 6,632,227 B2 | 10/2003 | Adams | |
| 6,663,639 B1 | 12/2003 | Laufer et al. | |
| 6,695,198 B2 | 2/2004 | Adams et al. | |
| 6,716,233 B1 | 4/2004 | Whitman | |
| 6,736,828 B1 | 5/2004 | Adams et al. | |
| 6,835,199 B2 | 12/2004 | McGuckin, Jr. et al. | |
| 6,835,200 B2 | 12/2004 | Laufer et al. | |
| 6,872,214 B2 | 3/2005 | Sonnenschein et al. | |
| 7,530,984 B2 * | 5/2009 | Sonnenschein et al. | 606/139 |
| 2001/0054636 A1 | 12/2001 | Nicolo | |
| 2007/0246507 A1 | 10/2007 | Sonnenschein et al. | |
| 2007/0276436 A1 | 11/2007 | Sonnenschein et al. | |

FOREIGN PATENT DOCUMENTS

| | | |
|---|---|---|
| WO | WO 01/67964 | 9/2001 |

* cited by examiner

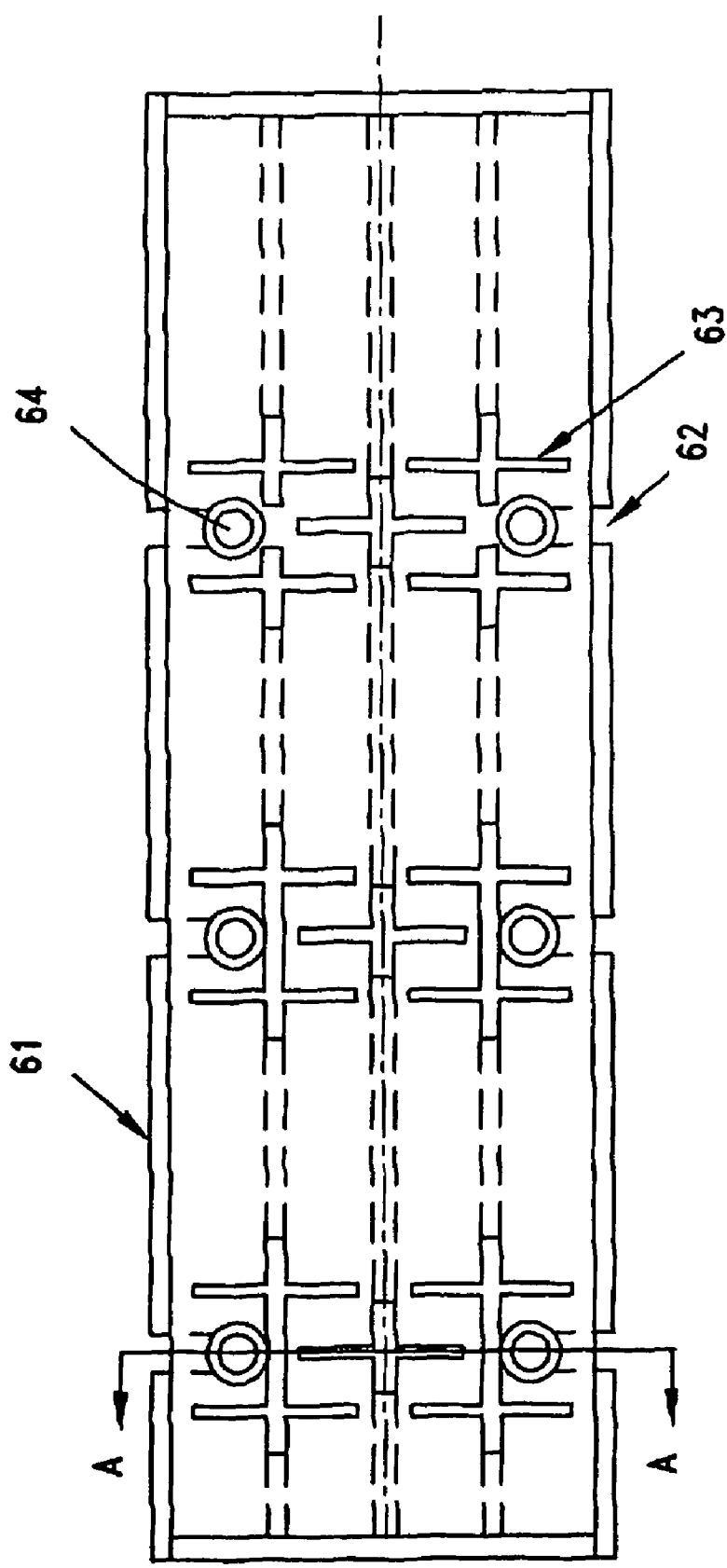

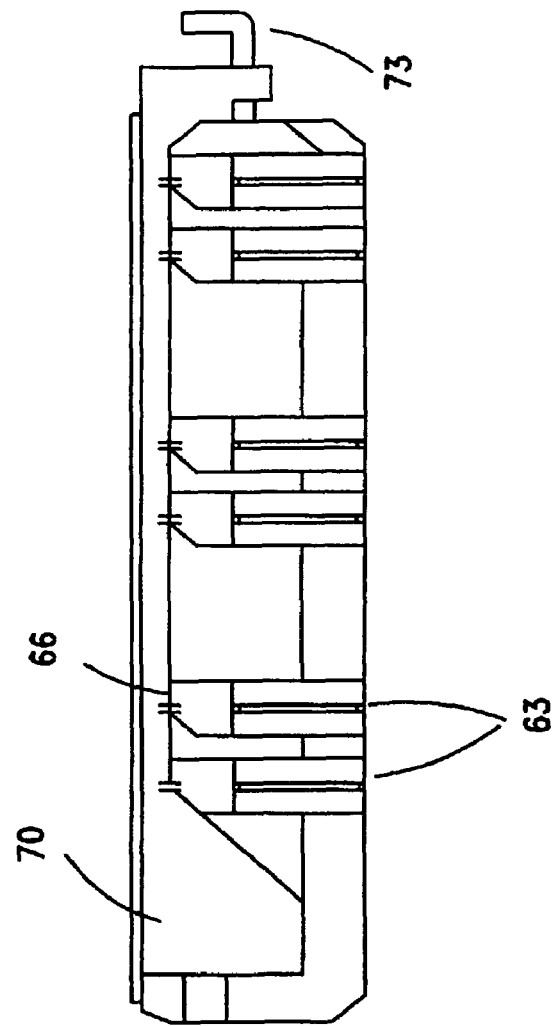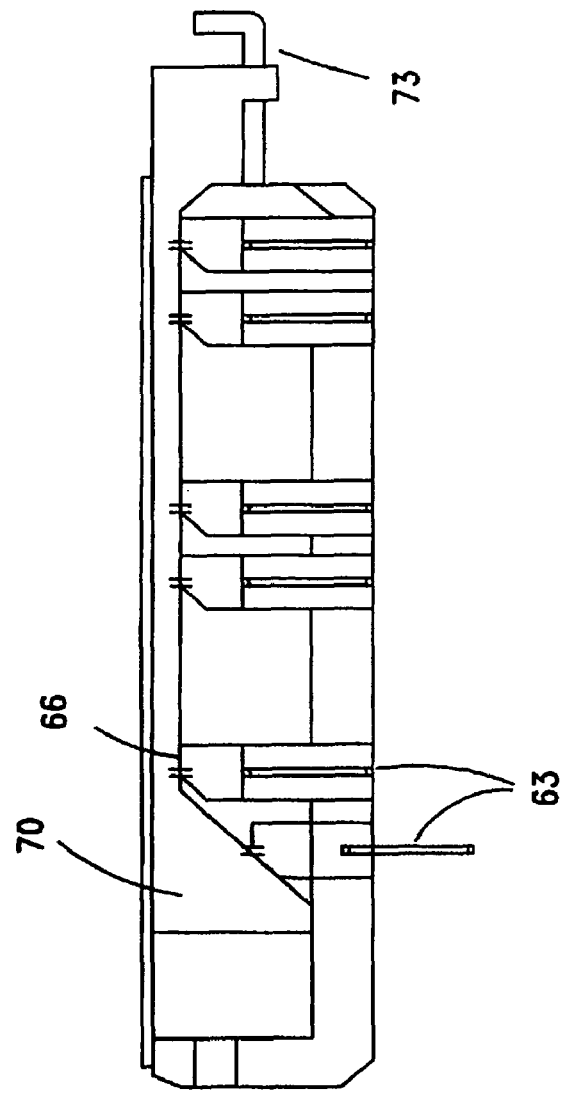

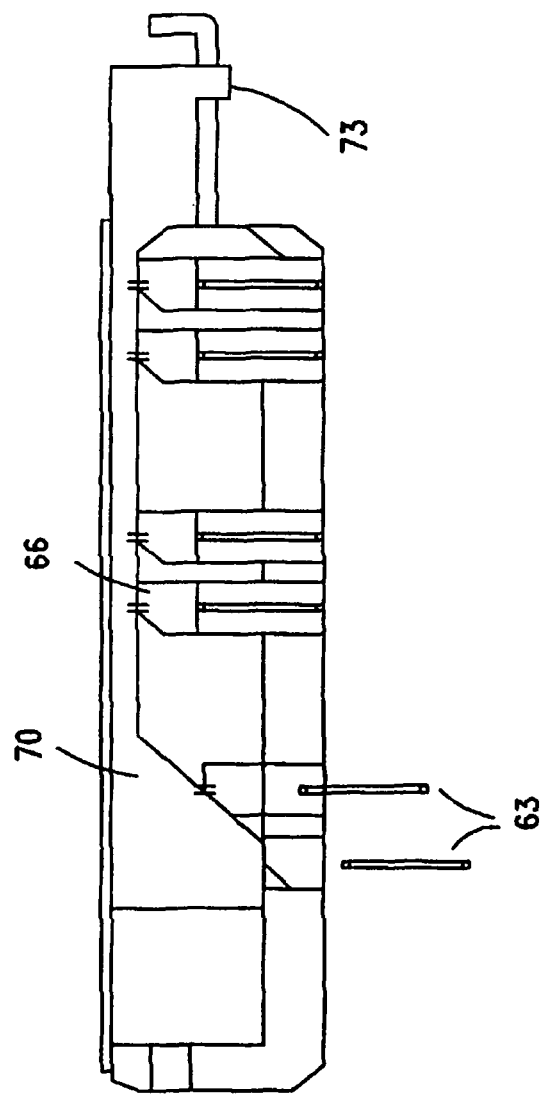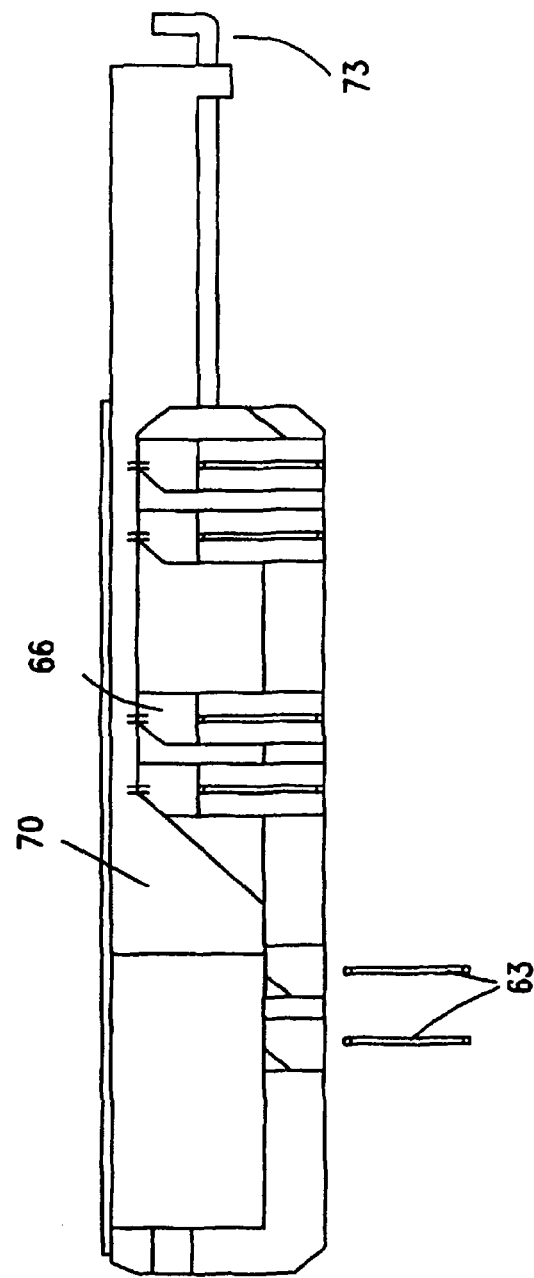

STAPLER FOR ENDOSCOPES

This application claims priority to the following application: this application is a continuation application of U.S. patent application Ser. No. 10/030,018, filed Sep. 11, 2002, now U.S. Pat. No. 6,872,214; which is a national stage submission under 35 U.S.C. §371 of International Patent Application PCT/IL01/00719, filed Aug. 2, 2001, and which claims priority from ISRAEL Application No. 139788 filed Nov. 20, 2000.

FIELD OF THE INVENTION

The present invention relates to endoscopic apparatus. More particularly, the invention relates to a stapler which is part of an apparatus and a method for using this apparatus to perform endoscopic surgical procedures.

BACKGROUND OF THE INVENTION

In recent years, surgeons have been increasingly using surgical staples instead of conventional sutures. Surgical staples and surgical stapling instruments have made many difficult procedures much simpler to perform, and significantly reduced the time required to perform them, thus allowing the patient to spend less time under general anesthesia.

In general, modern surgical stapling instruments for use on internal organs and tissues are comprised of a head containing a cartridge which holds the staples and a mechanism for ejecting the staples out of the cartridge, either sequentially or simultaneously, and driving them through the tissue. Typically, on the other side of the tissues to be stapled, there is an anvil, which deforms the staples into the shape required to hold the tissues together. The head and anvil together form the distal stapling portion of the instrument. There is a proximal portion which houses the actuator mechanism for firing the staples, and the mechanism for bringing the anvil and head to the desired distance and keeping them exactly aligned.

Many types of surgical stapling instruments have been devised for different surgical procedures. Typical designs of basic surgical staplers are disclosed in, for example, U.S. Pat. No. 5,129,570 and U.S. Pat. No. 5,630,541. U.S. Pat. No. 5,452,836 and U.S. Pat. No. 5,603,443 disclose staple designs in which the staple dispensing part and the anvil are separated.

In U.S. Pat. No. 5,403,326, Harrison, et. al. describe apparatus and a method for performing fundoplication of the stomach to the esophagus. The procedure involves introducing three separate devices, an endoscope, an esophageal manipulator, and a stapler through incisions in the skin into the stomach of the subject. The stapler consists of movable jaws at the operating end connected to a handle by an elongated body. One of the jaws contains the staples and the other the anvil. The stapler is introduced into the stomach, positioned with the tissue to be joined between its jaws and the staples are fired by pressing on a button located on the handle.

Bolanus, et. al. disclose in U.S. Pat. No. 5,571,116 another method of performing the fundoplication. In their method, a remotely operable invagination device is introduced transorally into the stomach through the esophagus. After manipulating and clamping the tissue of the fundus and the lower esophagus in the desired manner, a second instrument, a remotely operable fastening device, is introduced. The fastening device consists of a handle containing various levers, etc. to actuate the device, an elongated flexible portion of sufficient length to reach the position at which the operation is to take place, and a stapler at the distal end of the elongated portion.

The stapler is comprised of a cartridge frame, which contains a staple-containing cartridge and the mechanism for ejecting the staples from the cartridge, and an anvil pivotally connected to the distal end of the cartridge frame. To carry out the procedure, the fastening device is inserted with the anvil closed to a point beyond that at which the stapling is to be carried out. The anvil is then allowed to be pivoted open and the fastening device is moved proximally, capturing the tissue to be stapled between the staple cartridge and the anvil. Using the levers on the handle the anvil is again closed clamping the tissue to be fastened. Staple ejectors are then activated driving the staples out of the cartridge, through the tissue, and against the anvil where they are bent into the desired shape. The anvil is again biased open, the fastening device is moved distally to free it from the tissue, the anvil is again closed, and the device is withdrawn.

U.S. Pat. No. 5,197,649 and U.S. Pat. No. 5,395,030 describe surgical staplers that have been developed for connecting the severed edges of tubular tissue such as that of the intestines.

Many other stapler designs are disclosed in the prior art. Many of these are specialized devices that are suitable for performing only the type of procedure for which they have been designed. Most of these are very difficult and time consuming to work with, requiring a great deal of skill to manipulate the tissues and the stapling device.

A basic consideration in the design of all staplers is the fact that it takes a substantial force to bend the staples. Consequently, at the time the staples are fired, the anvil and the head must be clamped rigidly together, or the force will cause them to separate, and the staples will not fully bend. In addition, for the staples to bend to the shape required to hold the tissues together, the anvil and the staple dispensing part must be aligned precisely. Because of these limitations, the distal stapler holding and anvil portions of the device are typically rigidly pivotally connected together in existing staplers. In staplers where the anvil and staple dispensing parts are separate, clamping is done manually at the desired location for stapling, which often necessitates physical manual contact with the tissues to be stapled together.

With current stapling methods, it is impossible to hold the aforementioned parts rigidly together unless they are rigidly or pivotally connected at the time of placement.

It is highly desirable to have a totally flexible connection between the anvil and staple dispensing portions of the instrument. In laparoscopic or open operations, a totally flexible connection will allow stapling in hard-to-reach places. Moreover, a totally flexible stapling instrument could be combined with a flexible endoscope, which will permit the instrument to be passed through natural orifices, such as the mouth, anus, or vagina. Any number of procedures could then be performed without the need to fully anesthetize the patient, and without opening the abdomen. A non-exhaustive list includes: removal of broad-based colonic polyps and small cancers; endoscopic treatment of gastresophageal reflux disease (GERD), and full thickness biopsies of gastric lesions. All of which are hitherto often performed under the influence of a general anesthetic.

Because of the need to hold the anvil part and the staple dispensing part of the stapler together, a totally flexible connection is not practical, using existing methods.

It is an object of this invention to provide a surgical stapler which overcomes the drawbacks of prior art by providing a totally flexible connection between the staple holder and the anvil parts, at the time of insertion and placement at the surgical site, yet holding the staple dispensing part and the anvil part rigidly together and in precise alignment at the time of the firing of the staples.

It is another purpose of the invention to combine a stapling device made of two separate parts with a flexible endoscope, to achieve an instrument that can be used to endoscopically perform a variety of surgical procedures.

It is a further purpose of this invention to provide a device for performing endoscopic surgical procedures that improves over the devices of prior art in its ease of operation.

It is yet another purpose of the invention to provide a stapling device that is particularly suitable for use in a flexible endoscope for the treatment of GERD by fundoplication.

Other purposes and advantages of this invention will appear as the description proceeds.

SUMMARY OF THE INVENTION

In one aspect, the invention is directed towards providing a stapling device for a surgical endoscopic device provided with at least one flexible portion, comprising a staple-firing portion and an anvil portion, wherein one of said staple firing portions and one of said anvil portions are located longitudinally displaced from one another along the longitudinal axis of said endoscopic device, with at least a part of said flexible portion between them.

According to a preferred embodiment of the invention, the staple firing portion is located proximately to the proximal end of the flexible portion and the anvil portion is located on the distal end or tip of the flexible portion, although the positions of the two portions can be interchanged. According to a preferred embodiment of the invention, the flexible portion is an articulation section. According to one embodiment of the invention, the stapling assembly comprises one or more alignment and/or locking pins that can be extended or retracted from one part of the stapling assembly into a locking position in the second part of the stapling assembly. According to a preferred embodiment of the invention, the motion of the alignment and/or locking pins is accomplished by employing a dual rack and single pinion system.

According to another preferred embodiment of the invention, the parts of the stapling device are in correct working relationship when two alignment and/or locking pins that are stored in the anvil portion are extended and engage and lock into receptacles on the staple firing portion.

In another preferred embodiment of the invention, the alignment and/or locking pins are replaced by screws that are rotated by an arrangement of gears actuated by rotation of a screw drive cable. The parts of the stapling device are in correct working relationship when two screws that are stored in the anvil portion are extended and engage and screw into receptacles on the staple firing portion.

According to another preferred embodiment of the invention, the endoscope employs a two-way articulation system. In this case, completely bending the articulation section using a fixed radius of curvature brings the two portions of the stapler into alignment.

In another embodiment, a four-way articulation section is used. In this case a positioning assembly comprising two separate elements, one of which is located near to the staple-ejecting portion, and the other near to the anvil portion, is provided to assist in bringing the parts of the stapling device into correct working relationship. The positioning assembly can employ ultrasonic, light, radio frequency, piezoelectric, or magnetic sources and detectors.

The staple firing portion comprises a staple cartridge containing one or a plurality of arrays of staples. Each array consists of one or a plurality of staples. The arrays of staples are fired by staple pushers actuated by cams actuatable by proximal means. The staple cartridge is indexable after the firing of each of the arrays of staples by the action of a proximal actuating device.

In a preferred embodiment of the invention, there are either two or three arrays of staples and there are five staples in each array. Of course other arrangements with a different number of arrays and/or of staples can be provided. Windows are preferably provided on each side of the staple cartridge, to assist in locking it in place after indexing.

Preferably, but non-limitatively, the device of the invention comprises safety means for disabling the operation of the staple-ejecting device when the two separate elements of the positioning assembly are not aligned.

In a preferred embodiment of the invention, the alignment and/or locking pins are manufactured such that the pin tips can be broken by the force exerted by the operator, e.g., a force applied on the mechanism designed for unbending the articulation section.

All the above and other characteristics and advantages of the invention will be further understood through the following illustrative and non-limitative description of preferred embodiments thereof, with reference to the appended drawings.

BRIEF DESCRIPTION OF THE DRAWINGS

FIG. 6A shows the layout of the cartridge holder body of FIGS. 5A and 5B;

FIG. 8A is a side view of the cartridge body of FIG. 6A, showing an activation cam;

FIGS. 8B, 8C, and 8D illustrate the firing of the staples;

DETAILED DESCRIPTION OF PREFERRED EMBODIMENTS

Figure 1:
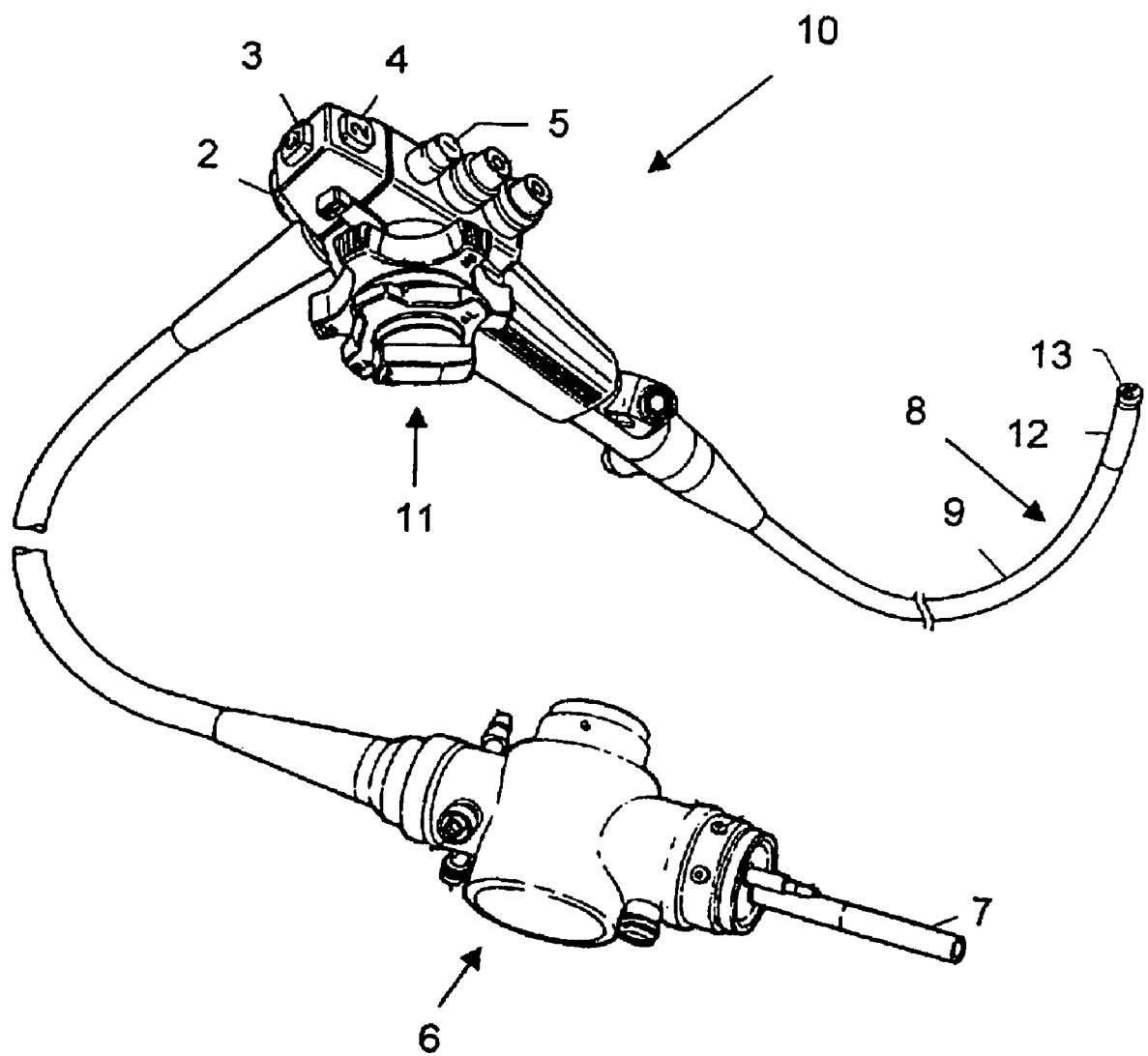
FIG. 1 schematically illustrates a conventional endoscope.

The invention will now be further explained through the illustrative and non-limitative description of preferred embodiments. A conventional endoscope is illustrated in FIG. 1. This endoscope comprises several features, such as the operating switches, the angulation lock, etc., that may be present in the device of the invention, but that will not be described in detail in the description to follow, because they are conventional and well known to the skilled person. Thus, in the following description only elements needed to illustrate the invention will be described. Briefly, however, the endoscope illustrated in FIG. 1 and generally indicated at 10, is provided with a control section 11 provided with suction valves, locks, switches, etc., switches 2-5 being marked for illustration purposes. It also comprises a connector section 6, used to connect air and water inlets, light guides, etc., the light guide being indicated at 7, for illustration purposes. The insertion tube 8 consists of three separate sections: a flexible portion 9, an articulation section 12 and a distal end 13. The articulation section is shown in greater detail in FIG. 2A, which also indicates the distal tip 24 in which the distal end 13 resides.

Figure 2A:
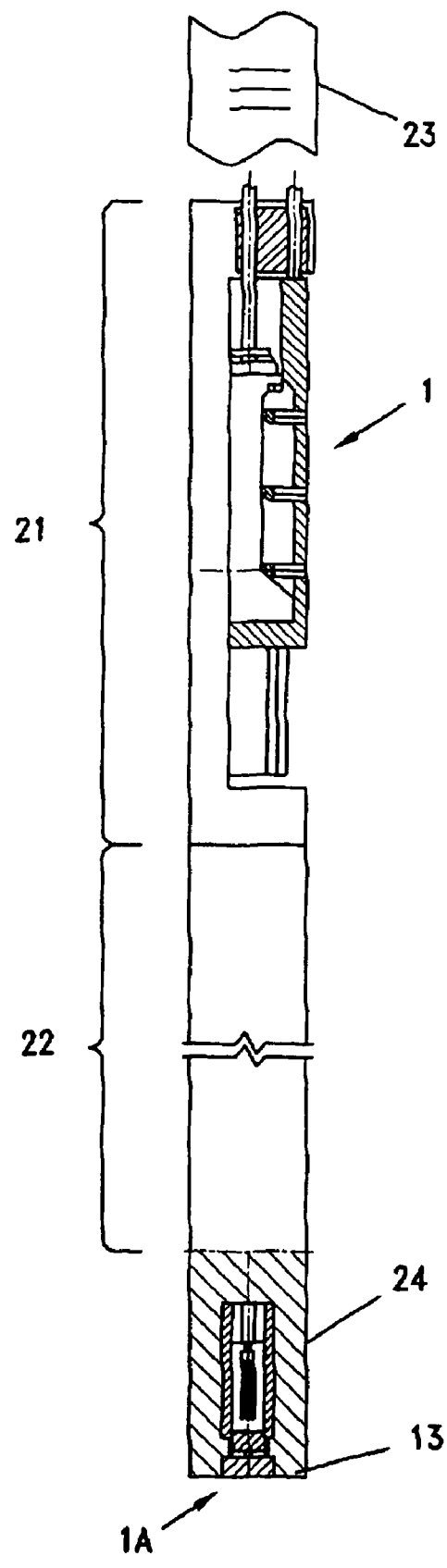
FIG. 2A schematically illustrates the fixed portion and the articulation distal portion of an endoscope, comprising a stapler consisting of an anvil portion and a staple ejecting portion containing three arrays of staples, according to a preferred embodiment of the invention.

Looking now at FIG. 2A, the distal portion of an endoscope embodying a stapler, according to a preferred embodiment of the invention is schematically shown. This portion comprises a staple firing mechanism indicated at 21 and an articulating section 22, and the distal tip 24. The section 12 of FIG. 1 is composed of the sections 22 and 24.

An endoscope that can operate together with a stapler according to the invention will now be described in greater detail.

Articulating section 22 is similar in design to that of conventional endoscopes, but in this example possesses several unique features. In order to simplify the alignment procedure and at the same time achieve maximum accuracy, a two-way articulation design has been chosen. This means that the articulating section is constrained to bend in one direction only (i.e. the tip of the endoscope can only bend from straight ahead to one side and back in a relatively fixed plane). Secondly, the device is able to bend up to 270° in order to carry out the required medical procedure, which is further than in conventional endoscopes. Finally, the articulating section is strong enough to provide a significant force against the tissues during fundus distension (described below with reference to the illustrative surgical procedure), clamping, and stapling. Of course, the stapler of the invention can be used with a variety of endoscopic devices, and is not limited to be used with any particular endoscope.

Figure 10A:
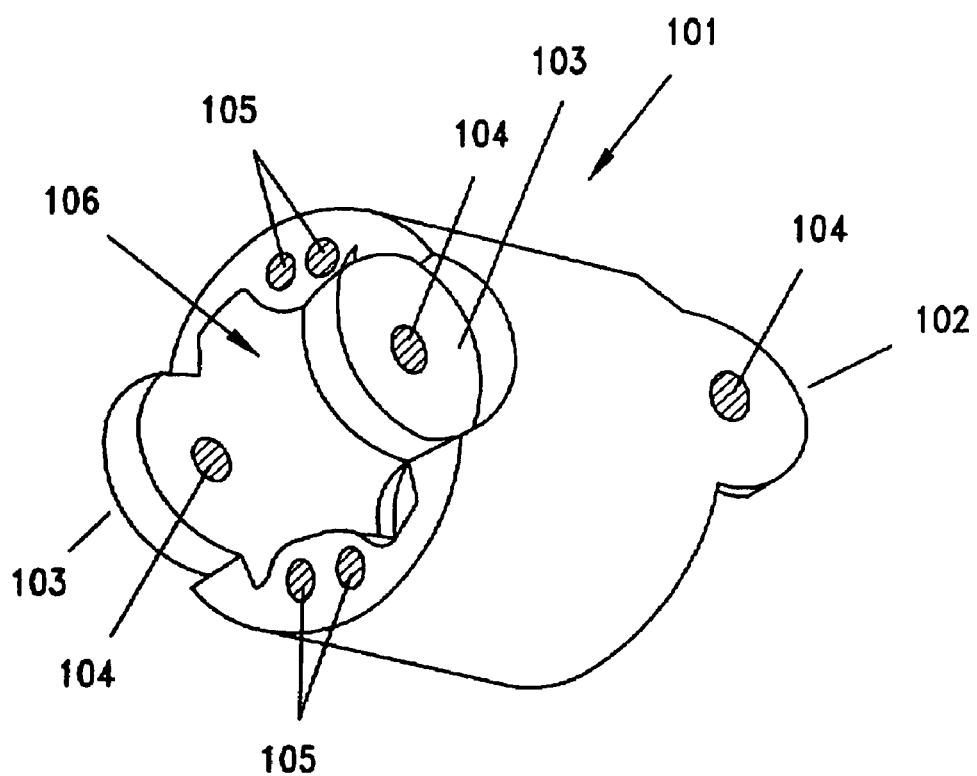
FIG. 10A shows a link of the articulation section of an endoscope.
Figure 10B:
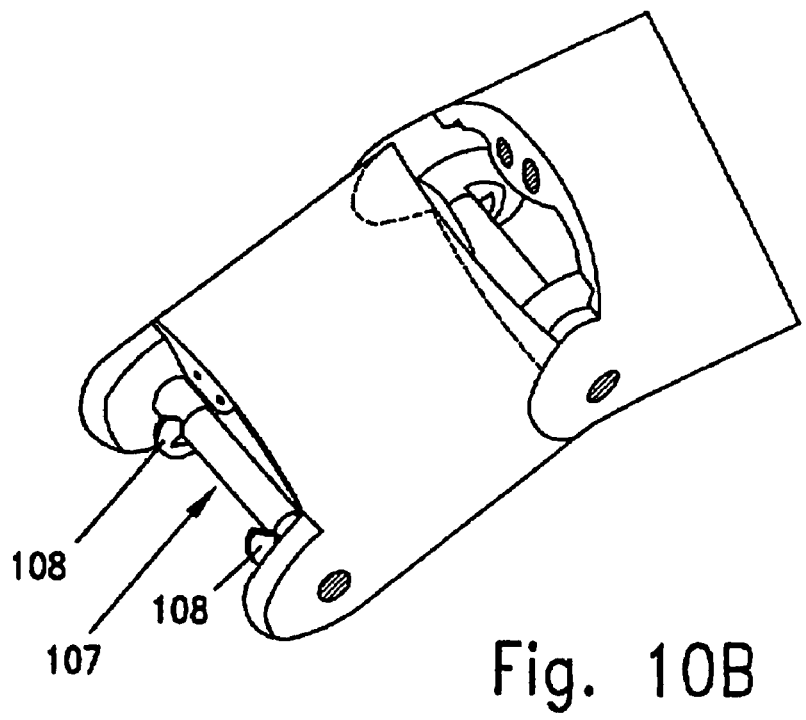
FIG. 10B shows the connection between two of the links shown in FIG. 10A.

The main features of the articulating section of the endoscope are shown in FIG. 10A and FIG. 10B. A typical link of the articulation section is generally shown as 101 in 10A. Each link is fabricated with a pair of circular lugs 102 with outer surfaces flush with the outer surface of the link at one end and a second pair of lugs 103 that are recessed by the thickness of lugs 102 at the second end. Each of said lugs is pierced by a hole 104. Four holes 105 are drilled in the link walls for the cables that are needed for articulation. A hollow region 106 through the center of each link allows the passage of optical, illumination, suction, etc. channels to the distal tip of the endoscope.

FIG. 10B shows the connection between two of the links of FIG. 10A. The pair of lugs 102 of the first link is slipped over the recessed lugs 103 of the second link. A swivel pin 107 is inserted through holes 104 in the lugs and retaining clips 108 may be added to complete the assembly. In another particular preferred embodiment of the device, retaining clips 108 are not provided.

Design parameters such as the length of the links, clearance (maximum bending angle) between links, and radius and maximum angle of curvature of the entire section determine the number of links that are joined together to form the articulation section. The outside ends of the first and last links are designed to interface with the rest of the endoscope and its distal tip, respectively.

The swivel pins contain cross-holes for the cables which must pass through them. These cross-holes and cables are not shown in FIGS. 10A and 10B.

In a preferred endoscope, the articulation section uses one pair of cables (or a single cable wrapped around a wheel located at the proximal end of the endoscope) for actuating the articulation. One cable passes through the hole in the link wall on the inside of the bending arc, and bends the endoscope into the bent position. The second cable is located opposite the first one, and unbends the section. The actuation mechanism is well known to persons skilled in the art, and need not be described here.

In another embodiment of the invention, a stapler is used together with a four-way articulation system. In a four-way system the tip of the endoscope can be moved in two mutually perpendicular planes. This gives more degrees of freedom of movement, but complicates the alignment procedure and necessitates the use of one of the alignment systems to be described below. Four-way systems are well known in the art and therefore will not be described here, for the sake of brevity.

According to a preferred embodiment of the invention, the stapler cartridge is positioned at the proximal end of the articulation section, 22. The stapler deployment system has a side firing design and requires an anvil which is located on the end of the distal tip. Both the stapler cartridge and the anvil module are replaceable and fit into receptacles on the shaft and distal tip. These receptacles are labeled 1 and 1A respectively in FIG. 2A. The stapling elements at 1 and 1A, together, form the entire stapling assembly, to be discussed in greater detail below.

Figure 2B:
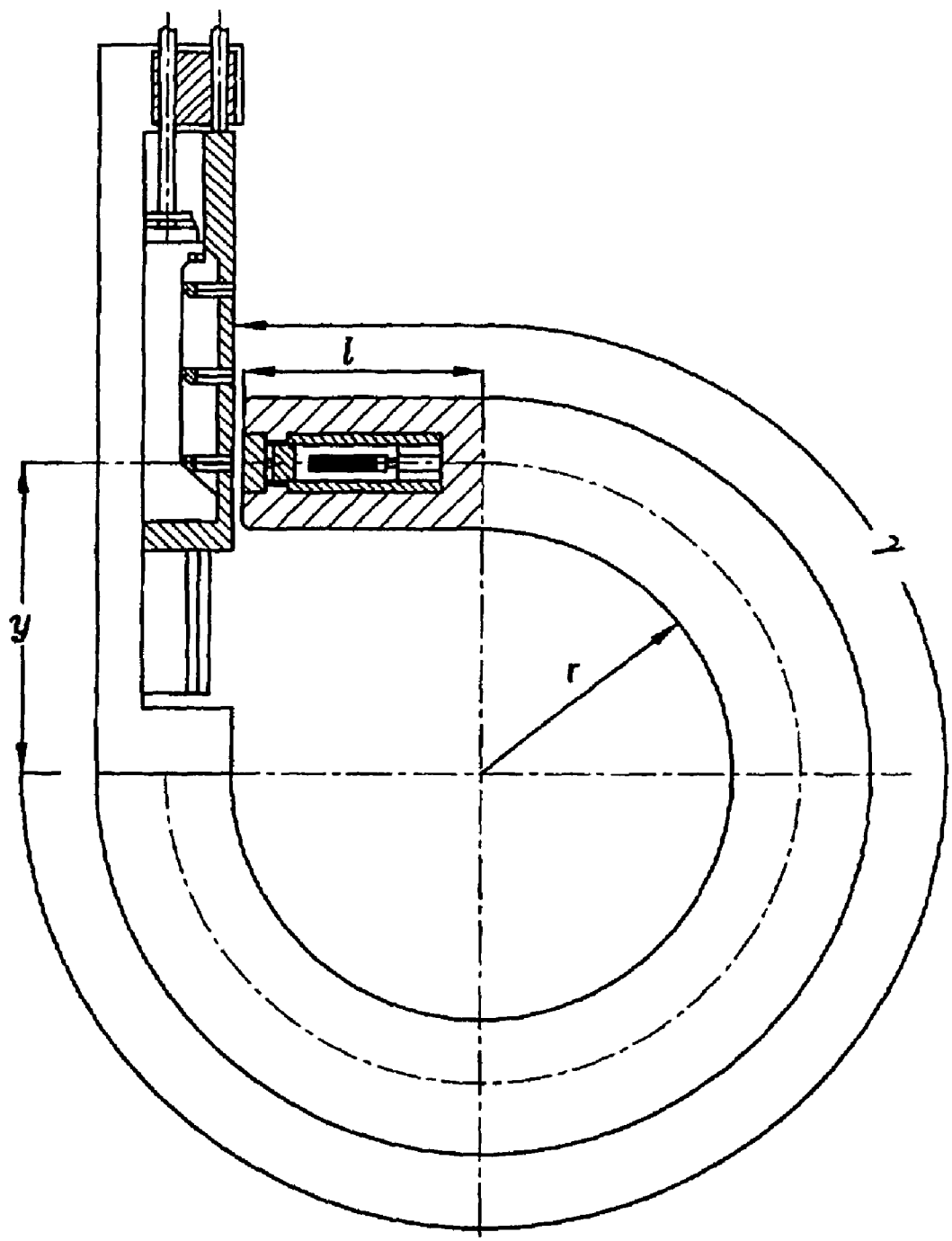
FIG. 2B schematically illustrates the articulation of the endoscope of FIG. 2A through its maximum bending angle.

FIG. 2B schematically shows the device of FIG. 2A in a fully articulated position. The articulation section 22 has been bent through bending angle α using fixed radius of curvature "r". The values of radius "r" and the length of the articulation section are determined by the fixed values "l" (length of the rigid distal tip) and "y" (the distance from the position at which the stapling is to be carried out to the proximal end of the articulation portion of the endoscope) in such a way that articulation of the device completely brings the two parts of the stapler assembly exactly into alignment.

Figure 2C:
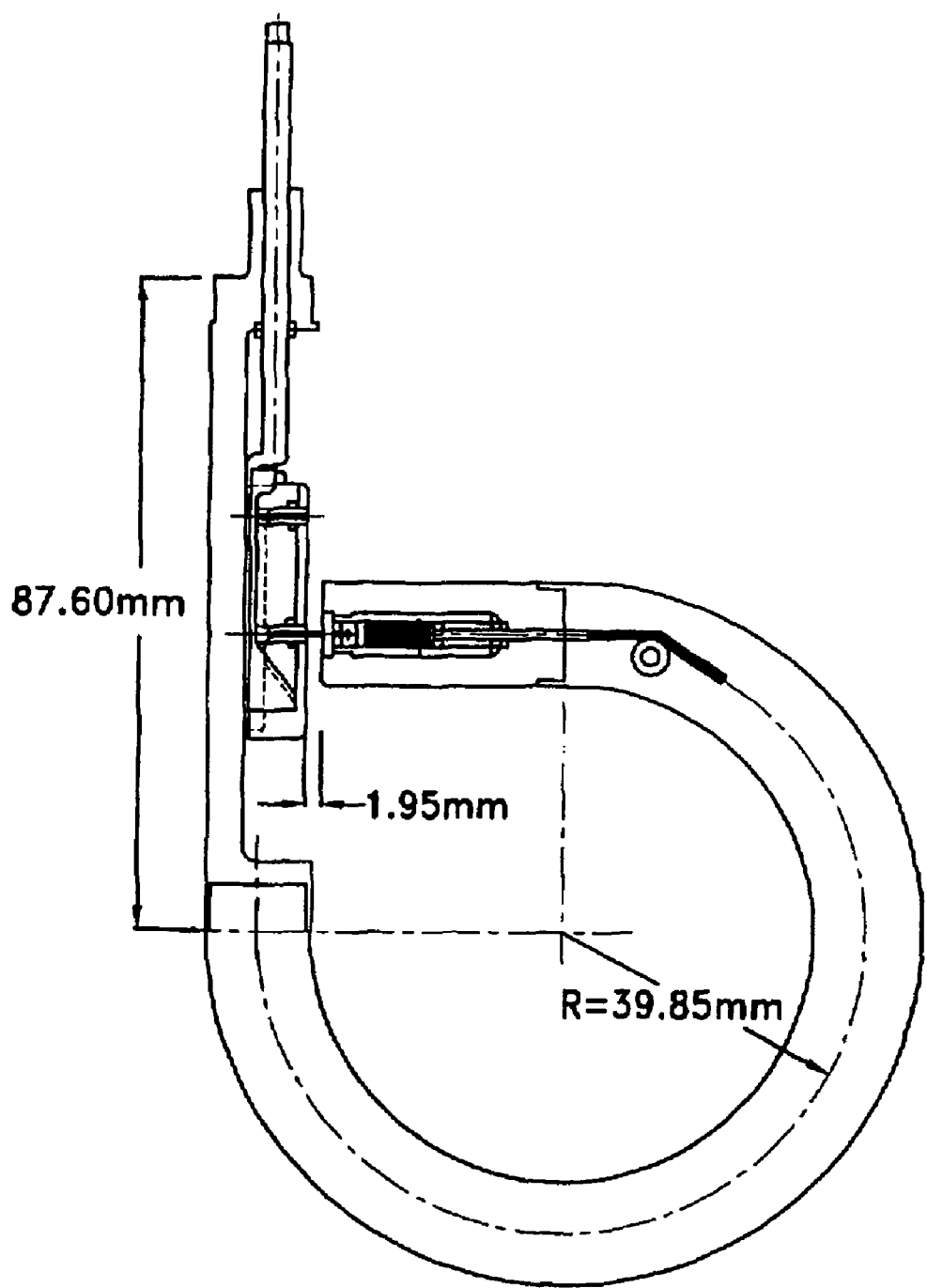
FIG. 2C schematically illustrates the fixed portion and the articulation distal portion of an endoscope, comprising a stapler consisting of an anvil portion and a staple ejecting portion containing two arrays of staples, according to a preferred embodiment of the invention.

FIG. 2C is the same as FIG. 2B for a different embodiment of the invention with illustrative, but not limitative, dimensions indicated. FIGS. 2A, 2B, and 2C all show the stapler cartridge in the first firing position.

Figure 3A:
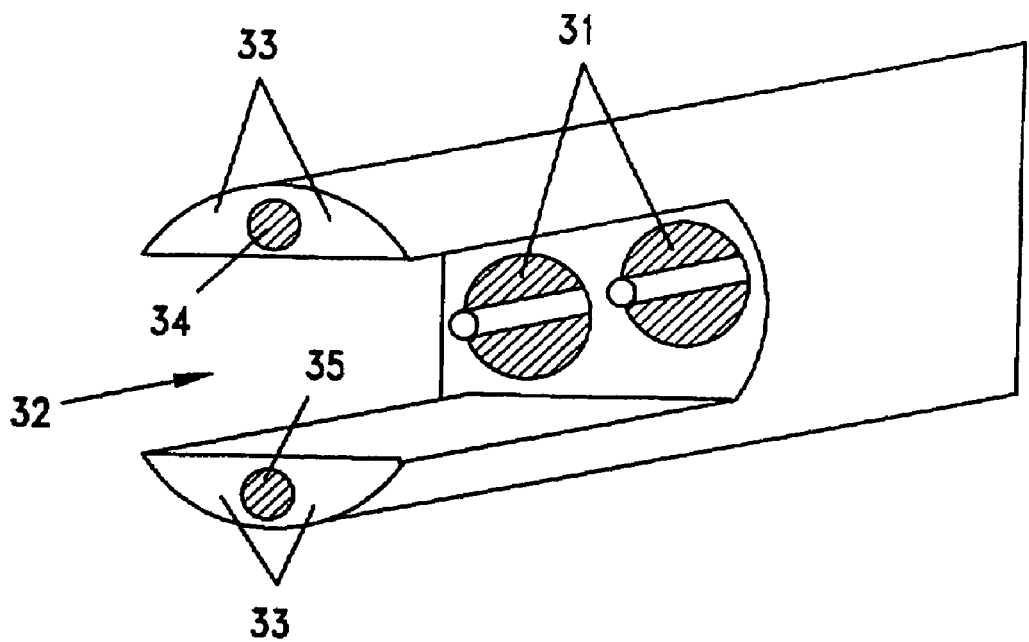
FIG. 3A schematically illustrates the distal tip of an endoscope, provided with a receptacle for the anvil section of a stapler, according to a preferred embodiment of the invention.

FIG. 3A schematically shows the distal tip of the endoscope (section 24 in FIG. 2A). The disposable anvil module of the stapler assembly goes into a receptacle schematically shown at 32. Two round reusable plungers and seals are part of the anvil holder and are shown at 31. A channel for suction, irrigation, or any other purpose is shown at 35. The imaging channel is 34 and 33 represents illumination fibers.

The skilled person will understand that other options can be provided and other configurations are allowed depending on the requirements of the endoscopic procedure to be performed. As one example, a transducer, receiver, or reflector can be placed at one of positions 33 for use in ultrasound positioning as described below.

Figure 3B:
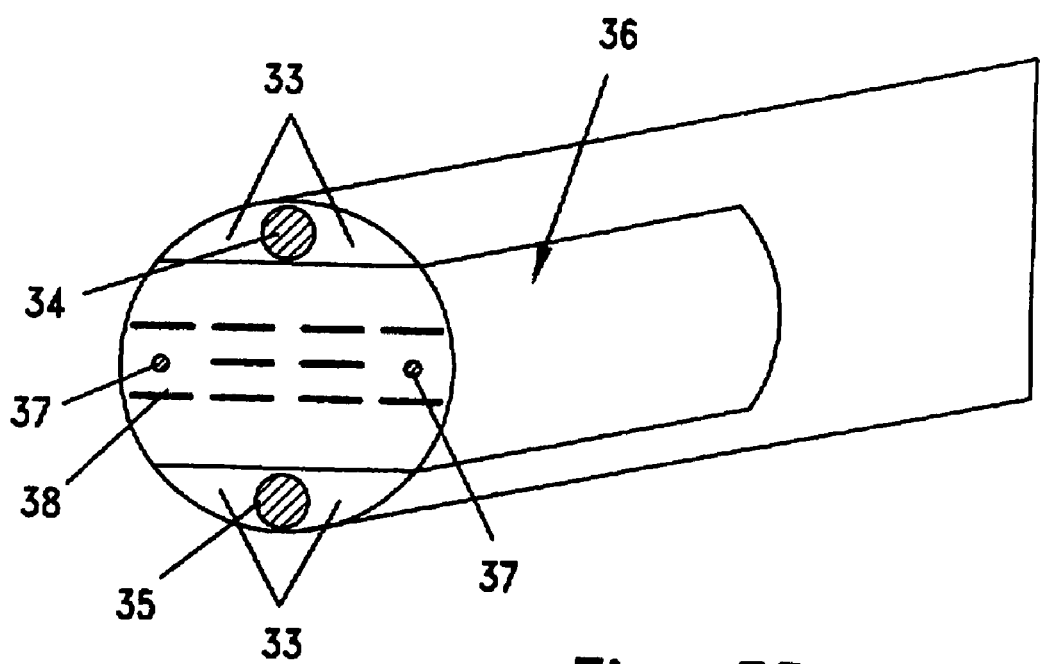
FIG. 3B shows the distal tip of the endoscope of FIG. 3A, with the anvil module of the stapler assembly in place.

FIG. 3B shows the distal tip of FIG. 3A with the anvil unit 36 in place. Numerals 33, 34, and 35 represent the same parts shown in FIG. 3A. Numeral 37 designates the holes through which the alignment and/or locking pins exit the anvil unit and 38 the depressions on the anvil unit face for curling the staples.

Figure 4A:
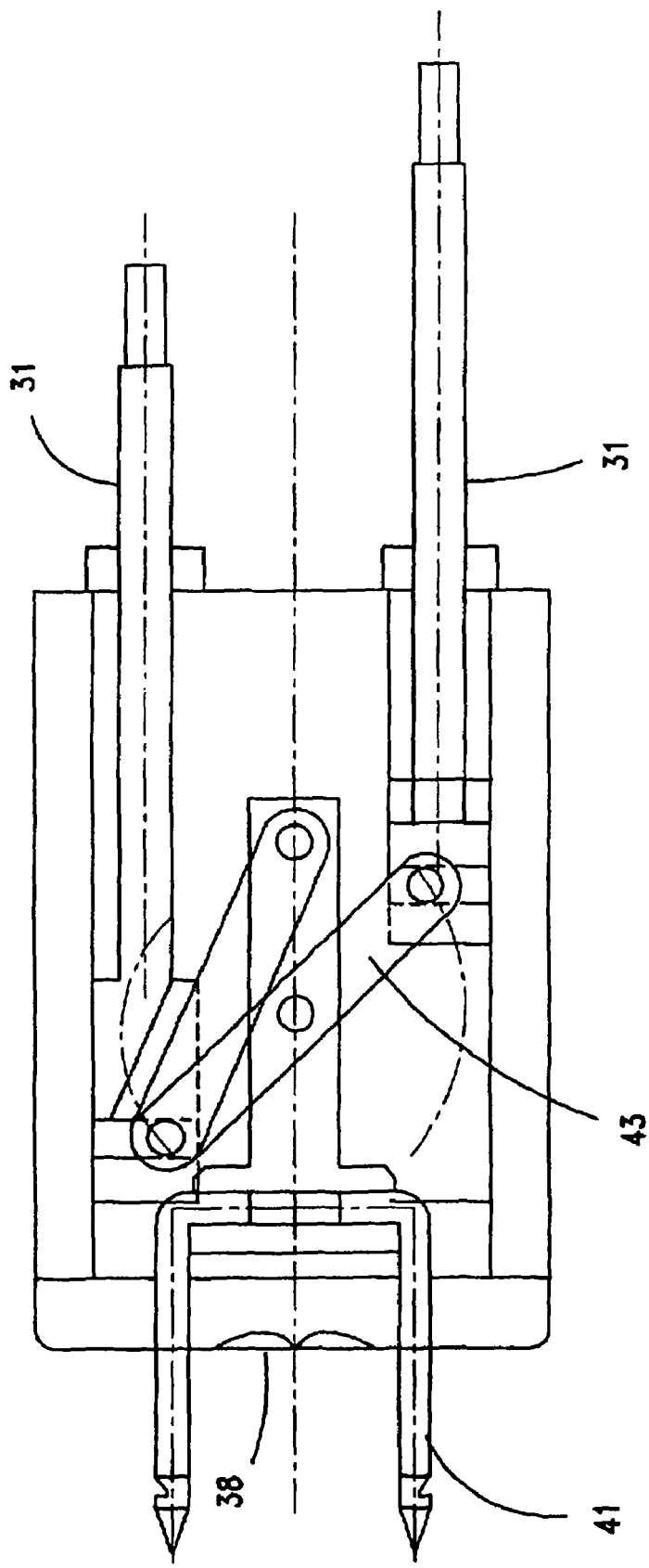
FIG. 4A is a cross-section showing the internal parts of the disposable anvil unit, according to a preferred embodiment of the invention.
Figure 4B:
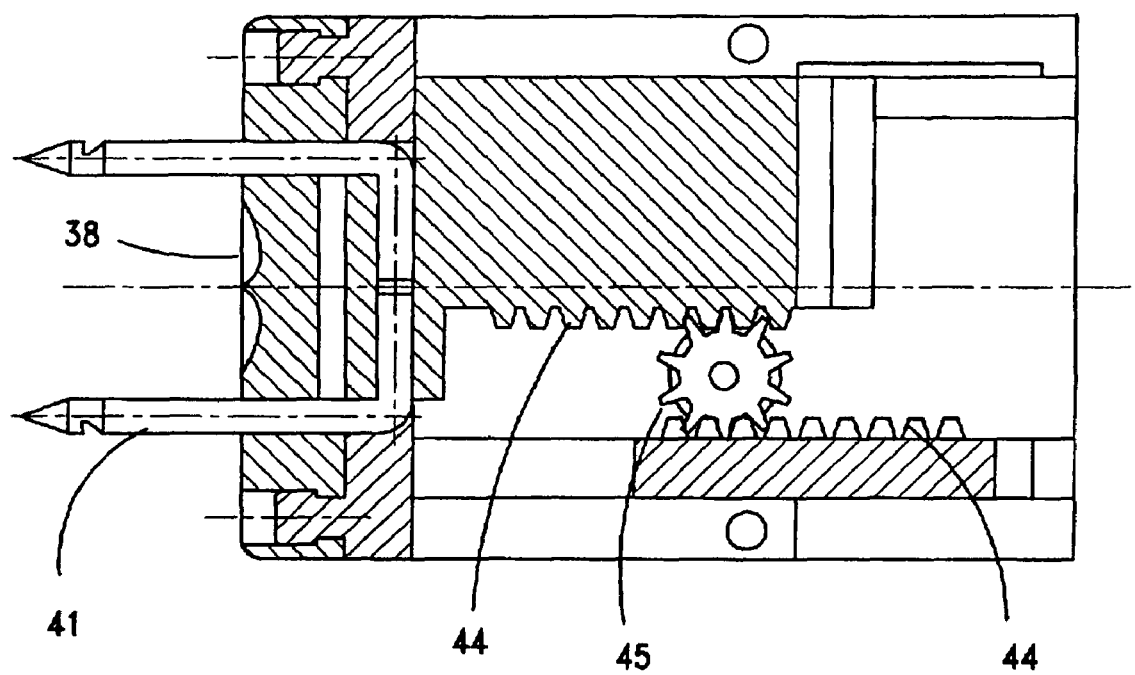
FIG. 4B is a cross-section similar to that of FIG. 4A showing the internal parts of the disposable anvil unit, according to another preferred embodiment of the invention.

FIGS. 4A and 4B are cross sections showing the internal parts of the disposable anvil unit that are needed to explain its operation. Two different systems are depicted in these figures.

Figure 4C:
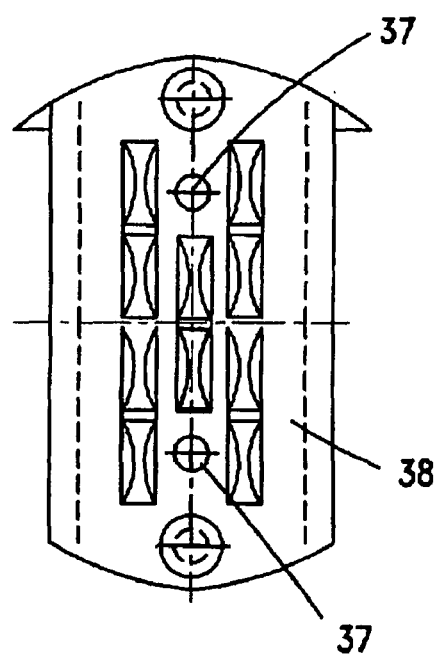
FIG. 4C shows the face of the anvil unit of FIG. 4A or FIG. 4B.

In FIG. 4A, the actuator mechanism 43 is employed to advance and retract the retention/locator pins. FIG. 4B depicts another preferred system. Within the support housing is located a dual rack 44 and single pinion 45 system to provide the desirable motion of the two retention/locator pins 41. Numeral 38 designates the depressions in the face of the anvil which cause the curling of the staples. The face of the anvil, showing the pattern of five staples used in the preferred embodiment of the invention, is shown in FIG. 4C. In this figure, 38 represents the depressions for curling the legs of the staples, and 37 are the holes through which the retention/location pins are projected. In FIG. 4A, numeral 31 designates the plungers that are part of the anvil holder and not of the disposable anvil unit.

Figure 5A:
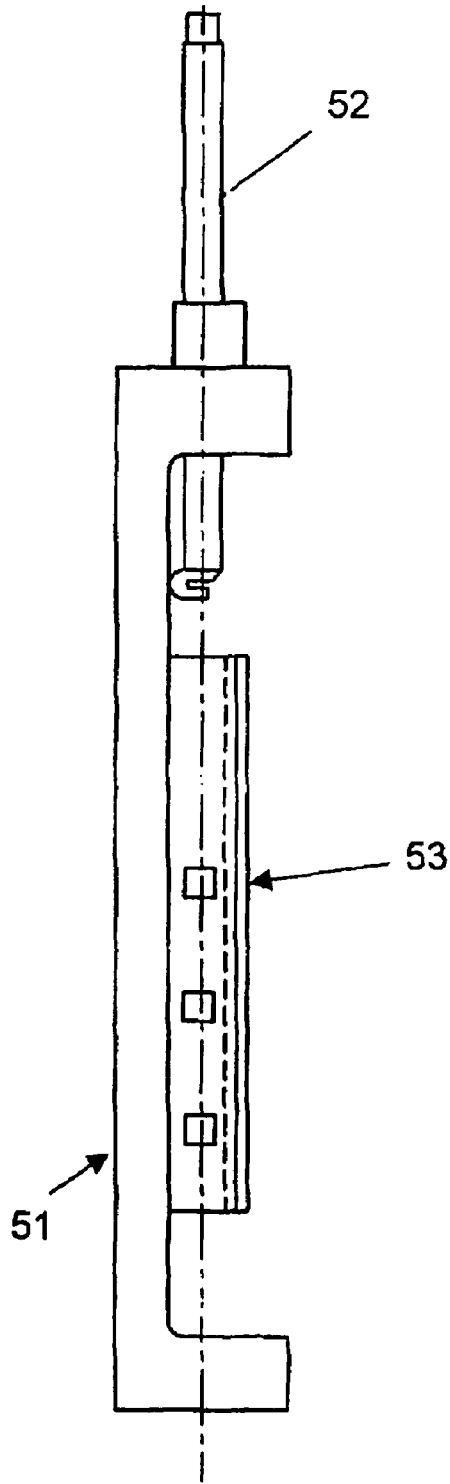
FIGS. 5A and 5B schematically show side and front views respectively of the staple cartridge holder, according to a preferred embodiment of the invention.
Figure 5B:
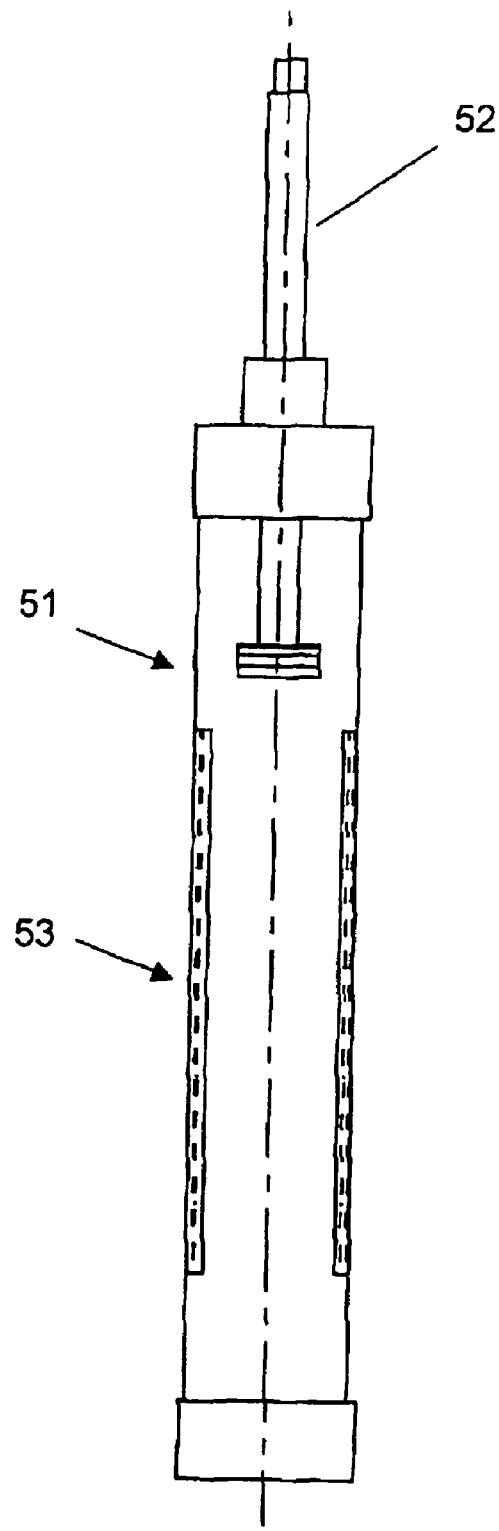

The second part of the stapler consists of a staple cartridge holder with disposable stapler cartridge located in the fixed portion of the endoscope shaft, proximate to the articulation section in the preferred embodiment of the invention. FIG. 5A is a side view and FIG. 5B is a front view that schematically show those parts that are located at 1 in FIG. 2A. The staple cartridge holder 51 consists of a tube of appropriate inside and outside diameters with a cutout in the profile. Within, the cutout is fitted with a piece of formed sheet metal (not shown) that forms a hermetic seal and retains the disposable staple cartridge 53 in the appropriate location with accurate index locations for the transfer of the staple cartridge for subsequent firings.

Attached to the tube and sheet metal subassembly is a plunger guide complete with a seal fitted with a plunger (collectively designated by the numeral 52). The plunger fires an array of staples when pulled in a proximal direction and then indexes the staple cartridge to the next position by a push motion in the distal direction.

Figure 6B:
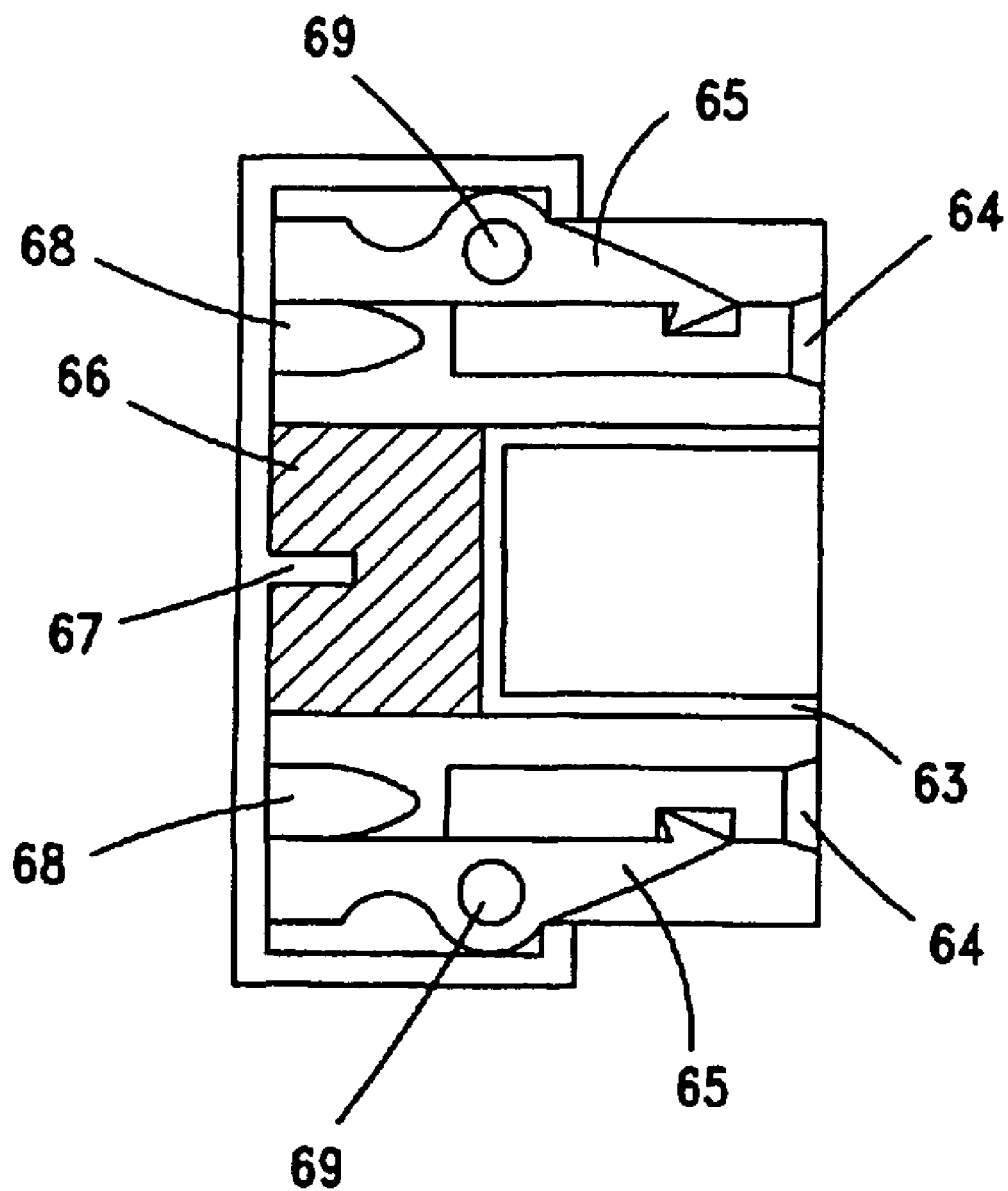
FIG. 6B is a cross-section taken along the A-A plane of the cartridge holder body of FIG. 6A.

The disposable cartridge case contains two subassemblies, the cartridge body that is illustrated in FIGS. 6A and 6B and the activation cam subassembly that is illustrated in FIG. 7A.

Referring to FIG. 6A, the staple cartridge is made of stainless steel or other suitable material such as a suitable plastic and consists of the cartridge body (generally indicated at 61) that, in a preferred embodiment of the experiment, retains three arrays each composed of five staples 63 and their respective pushers (shown in FIGS. 6B and 8A) at an appropriate distance. With each array of staples are two holes 64 complete with latches and springs, to bias the latches in the desirable direction for latching onto the location/retention pins that protrude form the anvil. Three windows 62, that are needed for indexing the cartridge, are present in each side of the cartridge body.

FIG. 6B is a cross-section of the cartridge body of FIG. 6A, taken along the A-A, plane, that schematically shows the major elements in this subsystem. In the figure, the numeral 64 designates the holes shown in FIG. 6A. This view shows schematically the beveled entrance to each hole, that allows for easier entrance of the pin into the hole and therefore pulls the two portions of the stapler into exact alignment as the pin enters the hole. The middle staple of the array is designated 63, and its pusher is indicated by the numeral 66. Numeral 65 designates the pawl and numeral 68 the leaf spring, the function of which is to lock the location/retention pin in place during the firing of the staples. In FIG. 6B, the numeral 69 designates the pivot of the latching pawl and a cutout in the pusher for the cam is shown at 67.

Figure 9B:
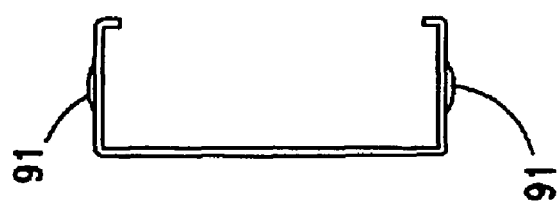
FIGS. 9A and 9B are respectively side and top schematic views of the housing of the stapler cartridge.
Figure 9A:
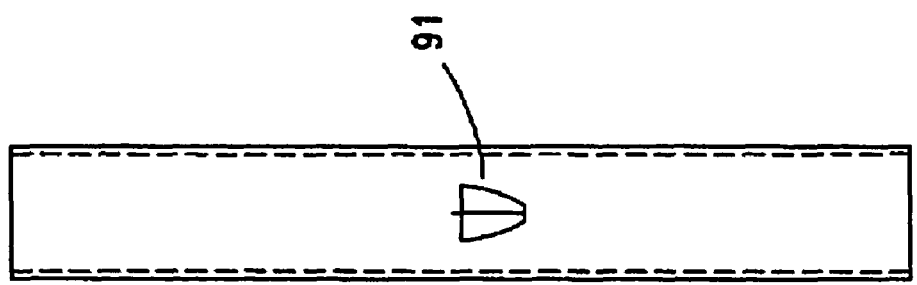

The cartridge has a sheet metal housing that encases it on the three sides and holds the cartridge together and keeps all the activation cams in place. The housing is shown in a side view in FIG. 9A and in a top view in FIG. 9B. It has two angled portions 91 that lock into one set of windows on the cartridge housing, to prevent the cartridge from moving proximally while the cams fire an array of staples, and which are then used for accurate location to the next position when indexing distally.

Figure 7:
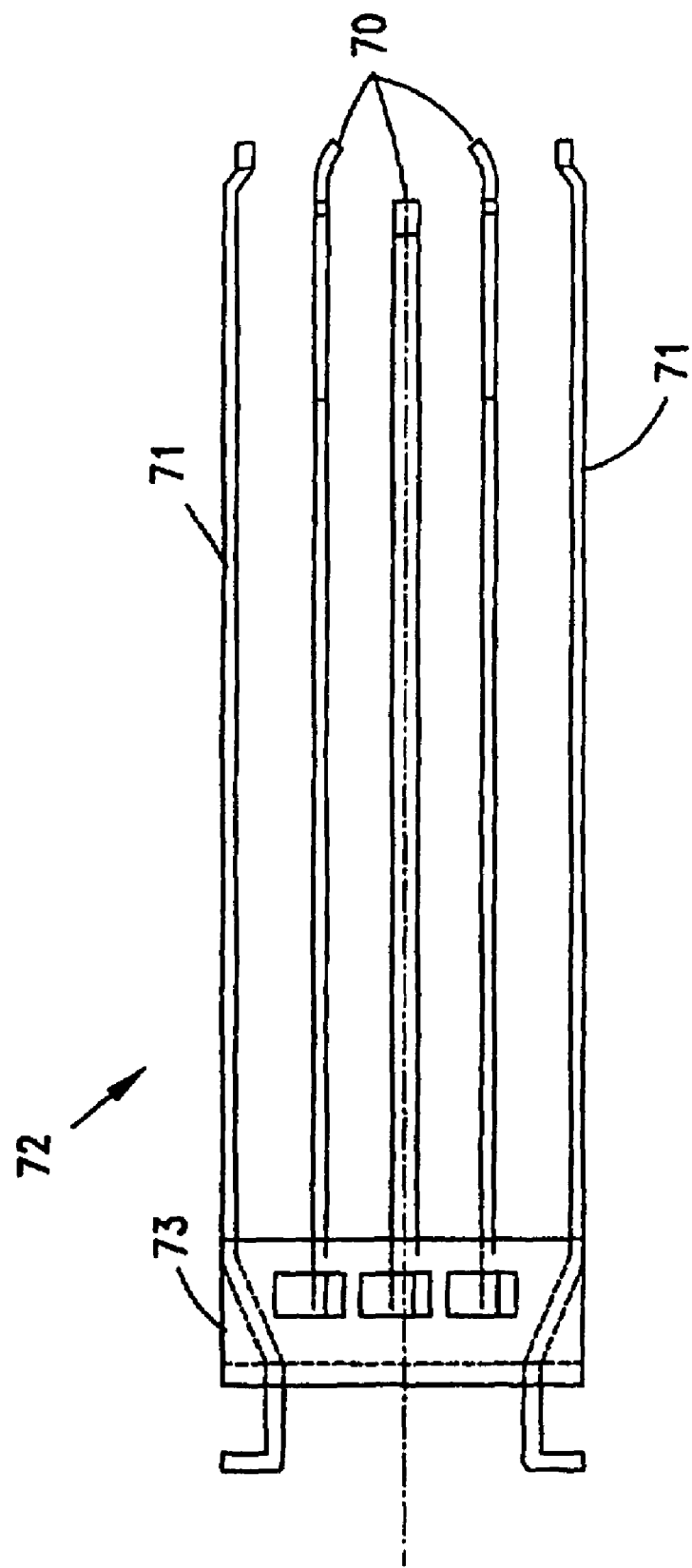
FIG. 7 shows the activation cam subassembly of the stapler cartridge of FIG. 6A.

The activation cam subassembly, shown generally in top view at 72 in FIG. 7, consists of three angular cams 70 that activate the staple pushers 66 that fire the staples 63 in FIG. 8A. FIG. 8A is a side view that shows the relationship between these elements. The three cams 70 are welded or otherwise retained to a cross member 73. The outside two of those cams also have tails that are formed slightly to ratchet into position in the cartridge for indexing into the next position.

Two other components 71, in FIG. 7, exist on the extreme outside. These are devices the function of which is to release the locking pawls and thus free the alignment/retention pins after firing of the array of staples. They are not welded to the cam assembly due to space constraints and because a dwell is required prior to initial movement. They are activated by the cross member 73 that is part of the cam assembly.

While in the above description of a preferred embodiment of the invention, a staple cartridge containing three pairs of windows for indexing and three cams for firing three arrays of five staples each is described, it should be clear that other embodiments can be provided containing different numbers of arrays and different numbers of staples per array, depending on the requirements of the procedure that is to be performed.

Figure 6C:
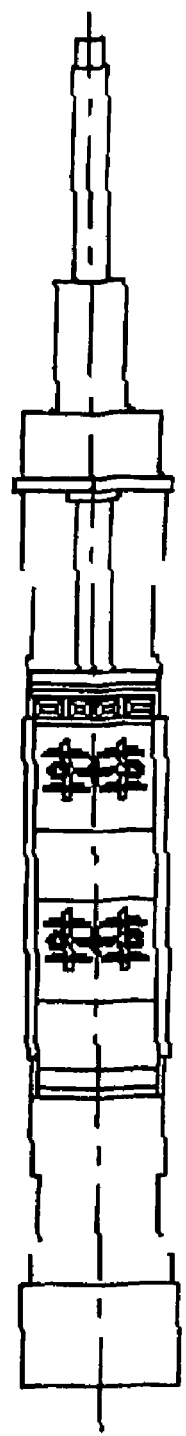
FIG. 6C is a face view showing the fixed portion of the endoscope containing a staple cartridge with two arrays of staples.

FIGS. 2C and 6C illustrate another preferred embodiment of the invention. In this embodiment the stapler cartridge contains two arrays each composed of five staples and their respective pushers. Two windows are present in each side of the cartridge body, to aid in indexing the cartridge. All the rest of the parts in the cartridge are as described above for the embodiment containing three arrays. It should also be understood by the man of the art that the positions of the stapler deployment system and the anvil can be interchanged and that the elements of the stapler can be located at different positions along the long axis of the endoscope. For example, one part of the stapler system can be located proximally from the connection between the articulation and flexible sections within the flexible shaft of the endoscope. It is even possible, in certain cases to reduce the radius of curvature of the device by placing the staple cartridge on one of the links of the articulation section, for example, if only one array of staples is to be fired.

The detailed description of the way in which the stapler system functions will be given below with the schematic description of a typical surgical operation that can be performed using the device of the invention, i.e. the fundoplication operation designed for the treatment of GERD.

Positioning markings 23 may be located on the device (as indicated in FIG. 2A), at the extremity outside the patient, to provide information on the location of the device that has been introduced into the patient.

Endoscopic vision means can also be provided. FIGS. 3A and 3B schematically show the distal tip of the endoscopic device. Regions 33 are the illumination channels, 34 is the image channel, and 35 is the irrigation/suction/ultrasound channel. Placement of imaging means at the distal tip assists in guiding the device to the desired position in the body lumen and allows imaging of the area during the performance of the surgical procedure. A second optical image can be provided. This image will be a view through a clear portion of the stapler and will show the staples as they are passed through the tissue and bent closed. Optical systems of conventional endoscopic apparatus can be employed. The endoscope may contain two or more separate optical channels that produce two or more distinct views. Preferred endoscopic optical systems are described in copending International Patent Application PCT/IL01/00238, Filed on Mar. 12, 2001 by the same applicant hereof, the description of which is incorporated herein by reference. However, the specific optical system employed is not relevant to the present invention, and many different optical systems may be provided by persons skilled in the art, and used together with the apparatus of the invention.

In the preferred embodiment of the invention described above, the alignment of the two separated parts of the stapler is accomplished by strictly mechanical means made possible by the use of a fixed radius of curvature and precise design and manufacture of the stapler and articulation section of the endoscope. In some alternative embodiments of the invention, however, it may be necessary to provide an aligning assembly consisting of two elements, one located near each of the portions of the stapler that, when brought into an alignment, assure that the portions of the stapler assembly are aligned and therefore permit the actuation of the stapler. According to one preferred embodiment of the invention, the elements of the positioning assembly are ultrasonic elements, i.e., an ultrasound transducer and a receiver or, alternatively a transducer and a reflector. A simple, well known to the person skilled in the art, analysis of the ultrasound signal received at the receiver makes it possible to determine the maximal signal, which corresponds to the exact alignment or, alternatively, to measure the distance between the transducer and receiver or reflector.

According to another preferred embodiment of the invention, one of the elements of the positioning assembly emits light and the other is a photosensitive element that translates the received light into a signal. Again, the maximal intensity of the signal indicates the maximal alignment.

According to still another embodiment of the invention, one of the elements of the positioning assembly is a piezoelectric transducer, and the other is a simple protrusion. Application of pressure by the protrusion on the piezoelectric transducer, via the thin tissue, generates an electric signal which, again, can be analyzed to determine its maximal value.

As will be appreciated by the skilled person, many other methods and systems can be devised for verifying the alignment of the system. For instance, using RF signals to determine the alignment position, or using a magnetic field generator on the one part, and a magnetic field positioning sensor on the other part. It should be mentioned that, in certain types of positioning assemblies, e.g., if it were desired to employ an RF assembly, it is not at all necessary that the two elements of the assembly be physically aligned viz., such that their physical centers are essentially aligned. When the alignment procedure does not rely on a physical, center-to-center matching, the two elements could be positioned differently on the two sections of the device, provided that when they generate an output signal representative of maximal alignment, elements 1 and 1A (FIG. 2A) of the stapling assembly are indeed physically aligned.

The endoscopic apparatus can be passed through any of the natural orifices, such as the mouth, anus, or vagina, and thereby avoid the need for the use of general anesthesia in performing procedures such as, for example, removal of colonic polyps and small cancers, full thickness biopsies of gastric lesions, and treatment of gastroesphageal reflux disease.

In order to illustrate the use of the apparatus of the invention, the medical procedure of performing an endoscopic fundoplication for the treatment of gastroesophageal reflux disease (GERD) has been chosen as an illustrative, but not limitative example. The symptoms and treatment of GERD have been extensively described in the art and are also discussed in the aforementioned International Patent Application, and will not be discussed here in detail, for the sake of brevity.

The device of the invention has three distinct areas of operation: 1) the introduction procedure, to position it in the desired location prior to the mechanical operation; 2) the mechanical operation of the device, to distend the fundus of the stomach and to bring both parts of the stapler into exact alignment prior to the surgical operation; and 3) the surgical operation involving the stapling of living tissue. These operations will now be described in detail.

The Introduction Procedure

Figure 13:
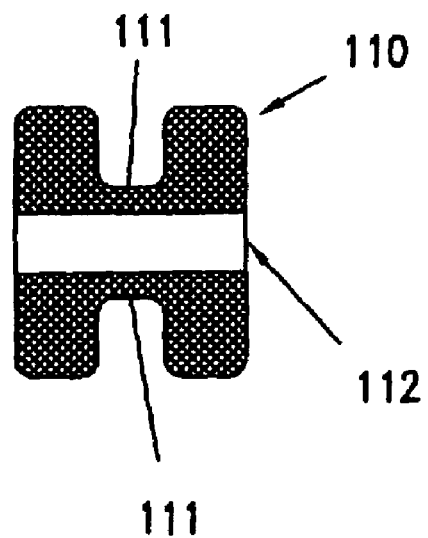
FIG. 13 is a biter, used to hold the endoscope in the mouth of the patient.

The procedure through which the endoscopic device is introduced into the stomach of the patient will be explained with reference to FIG. 2A, FIG. 2B, and FIG. 13. The endoscopic device is introduced into the esophagus of the patient through the biter. The biter, shown in cross-section in FIG. 13 and generally indicated at 110, has a biting portion 111 which is held between the teeth of the patient. The endoscopic device (not shown) is introduced through the biter via an appropriate opening 112. When in working position, the stapler module (at 1 in FIG. 2A) must be located at a distance which typically varies between about 5-6 cm from the gastroesophageal junction (GJ). The GJ is identified, when first introducing the device, by visual inspection via the viewing means of the endoscope. The total length of the device introduced at this stage is determined by reading the value indicated on the positioning markings 23, as also explained with reference to FIG. 2A. The endoscope is further advanced into the stomach. At this point, the stapler will be located at the desired distance above the GJ. The endoscope is now locked in position by fixing it to the biter using conventional clamping means (not shown).

Mechanical Operation of the Device

Figure 11A:
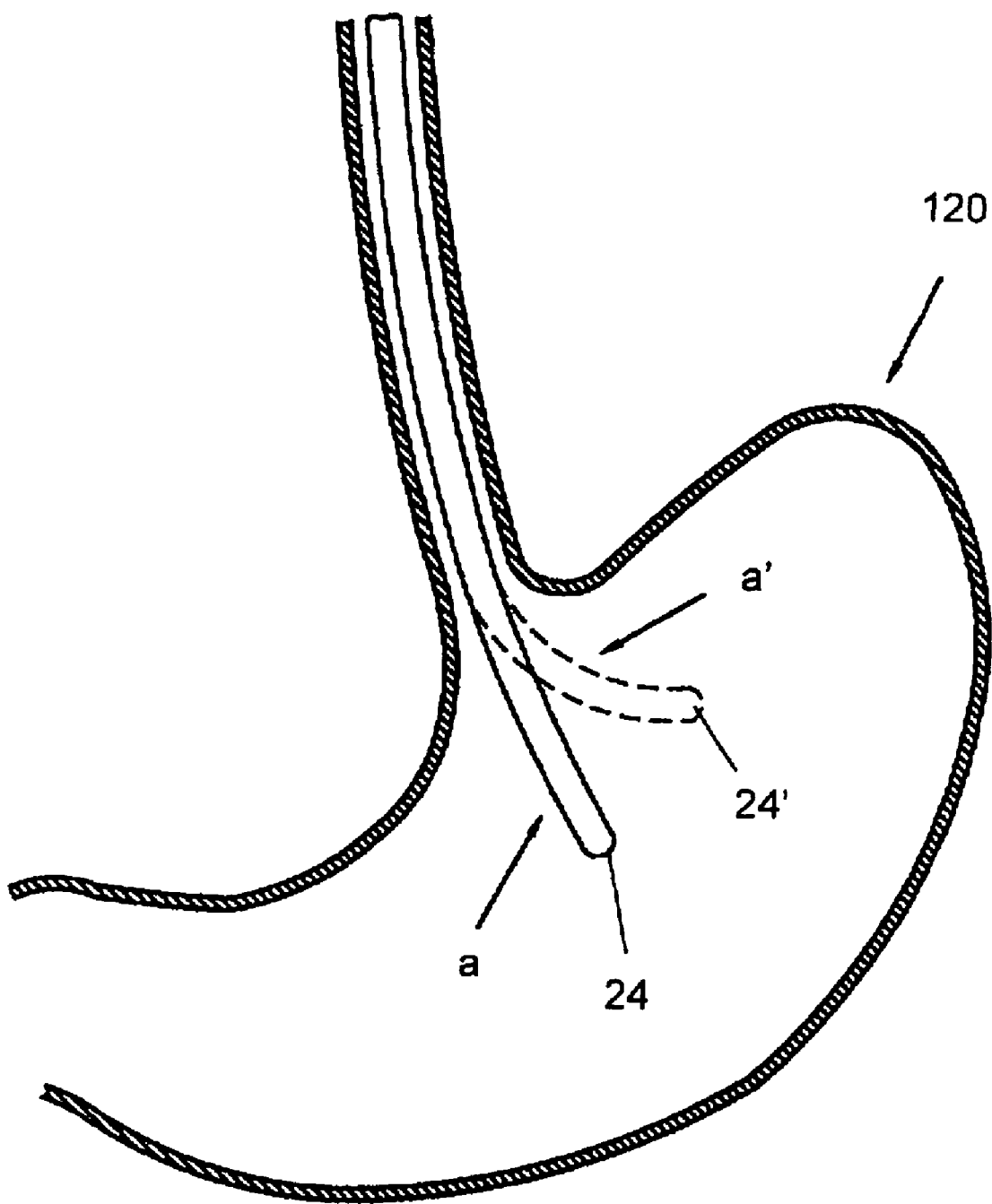
FIGS. 11A, 11B, and 11C schematically illustrate the mechanical procedure involved in the fundoplication using a device according to the invention.

The mechanical operation of the device involves the articulation of the bendable section of the device so as to engage the fundus of the stomach with the distal tip, and to move it toward the lower esophagus. This is schematically illustrated in FIGS. 11 (A, B, and C). In FIG. 11A, two positions of the device are shown, a and a'. Position a is the initial position after the device has been inserted the whole of its desired length as explained above. Position a' illustrates the beginning of bending of articulation section 22 (FIG. 2A) of the device, towards the fundus 120, the tip being indicated as 24'.

Figure 11B:
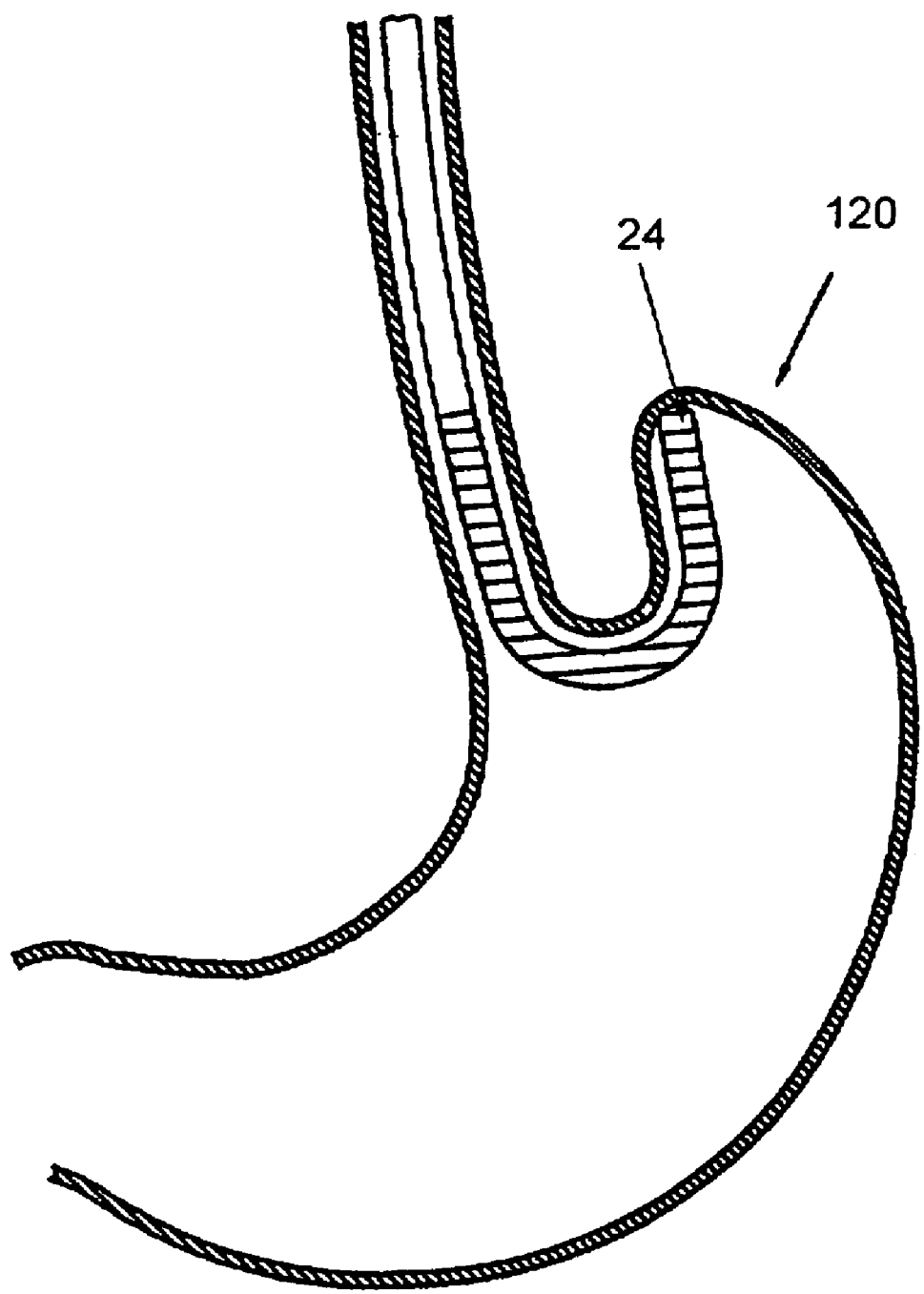

In FIG. 11B, the articulation of the device has proceeded to the stage in which the distal tip 24 has encountered the wall of the fundus 120 and started to pull it towards the lower region of the esophagus.

Figure 11C:
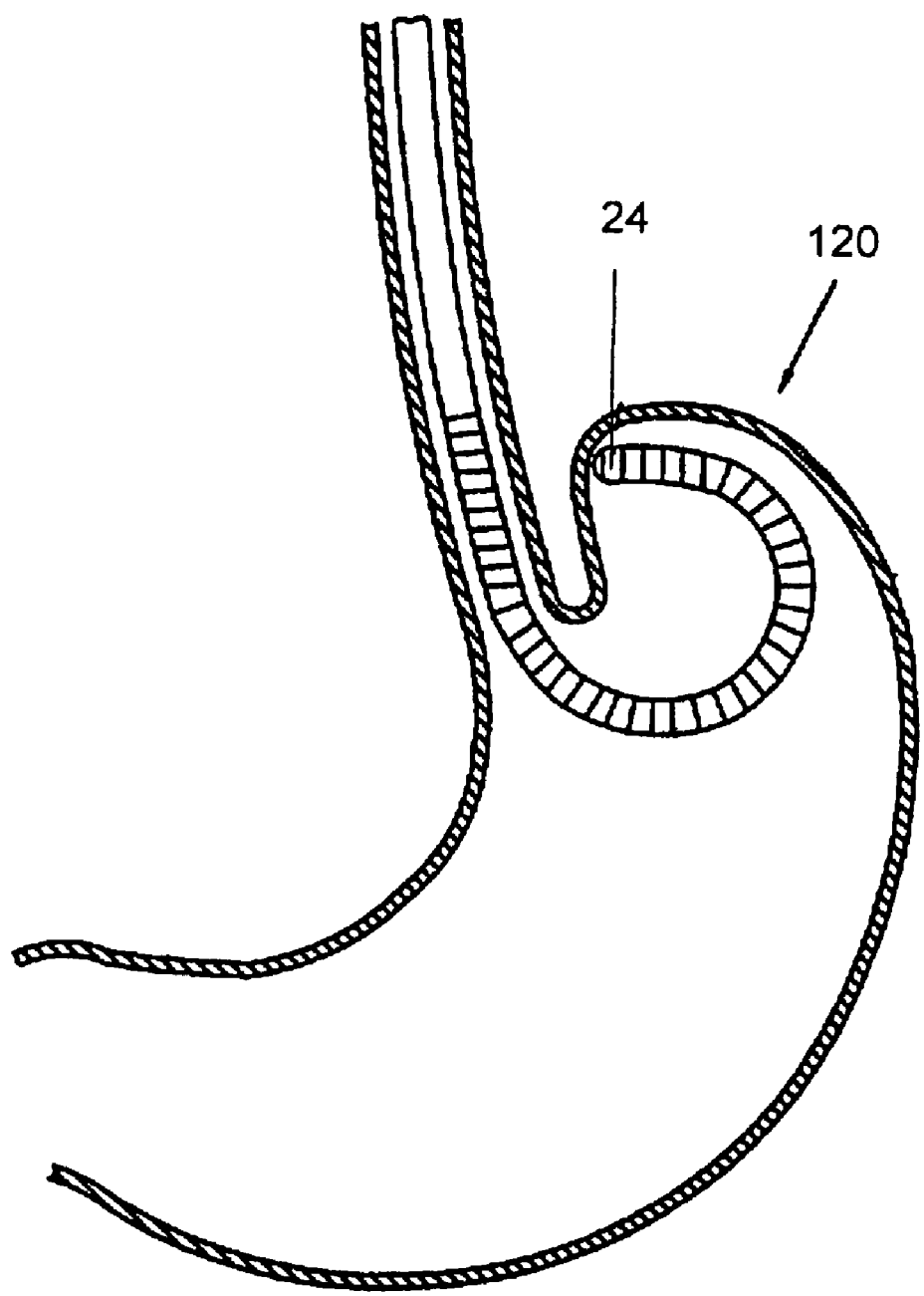

In FIG. 11C, the situation shown is that in which the articulation of the device has been almost completed, and the distal tip 24 has caused the fundus 120 to move from its original position to a position near the lower esophagus. In this position, the fundus is correctly positioned by tip 24 and it is possible to carry out the stapling together of the fundus and esophagus.

Figure 12:
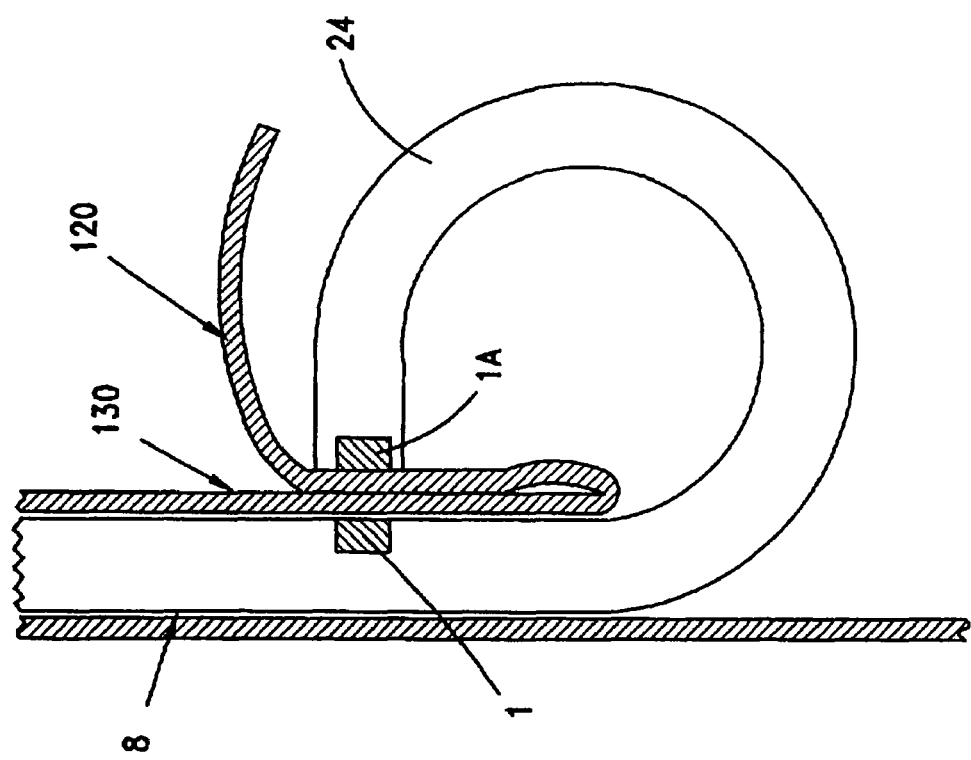
FIG. 12 schematically illustrates the positioning of the device prior to stapling.

FIG. 12 is a more detailed view of the situation when the articulation of the endoscope has been completed. Here is schematically shown the alignment between the staple cartridge 1, mounted in the proximal side of the articulation section of the endoscope within the esophagus 130, and the anvil 1A mounted on the distal end 24 within the fundus 120.

Surgical Operation

The surgical operation will be illustrated herein with reference to the stapling of tissue. In order to fasten the lower part of the fundus 120 (FIG. 12) to the lower part of the esophagus 130, by means of the stapling assembly, it is imperative that element 1 and element 1A be brought into the correct working positioned relationship, so that the staples, when fired, enter the anvil depressions accurately and perform their required task. Failure to bring the parts of the stapling assembly into the correct positioned relationship may be detrimental, as it will result in the staple not being correctly formed for retention and in a high risk of damaging the tissue where the stapling has been performed; furthermore, the aim of the procedure will not have been achieved, since the fundus has not been stapled to the esophagus.

As described above, in the preferred embodiment of the invention that utilizes the two-way endoscope, the design of the device assures proper alignment by articulating the device through its fixed bending radius. If so desired, the ultrasound or other techniques described herein are used to aid in alignment.

In other preferred embodiments of the invention that use four-way endoscopes, one of such means must be used to align the two sections of the stapler. The surgeon is able to verify the positioning, the proper distention of the fundus towards the esophagus, and the results of the stapling, by using the visual means provided at the distal tip of the endoscope. If the endoscope is furnished with an optical system according to the preferred embodiment of the invention described above, a second independent optical path is provided. Thus the surgeon can view the site from the side of the staple firing portion before and after the firing has been accomplished. Further as the two parts of the stapler are pressed together, the tissue is pressed between them and it is possible to see through the tissue allowing visual confirmation of proper positioning and alignment of the device.

Final alignment is accomplished by deploying the locking pins that are located in the anvil portion of the stapler. The method of accomplishing the deployment of the location/latching pins, in a preferred embodiment of the invention, can be understood by referring to FIGS. 4A, 4B and 6B. One distal cable is activated causing one of the plungers 31 to move forward. The plunger in turn causes the pins 41 to move forward by means of the rack 44 and pinion 45 gears. The pins pierce the tissue of the walls of the fundus and esophagus and are guided by the beveled entrance into the holes (64 in FIG. 6B) that are provided in the staple cartridge. Thus the final alignment of the two parts of the stapler is assured.

The techniques used to activate the plungers in the anvil section and also the firing plunger in the staple cartridge holder are well known to the man of the art and therefore will not be discussed here for the sake of brevity. As the pins advance into the holes in the staple holder, they are engaged and locked by the pawls (65 in FIG. 6B). The cable that advances the pins is now relaxed and the other cable is then activated to confirm the locking by the pawls, clamp the tissue, and provide the desired tissue gap.

Measuring the distance between the staple cartridge and the anvil by using ultrasonic techniques can be used to confirm the locking of the locking pins by the pawls. In another embodiment of the invention, an electronic safety mechanism is provided to prevent firing of the staples if the location/locking pins are not locked by the pawls in the stapler cartridge. The above mentioned International Patent Application describes a display system that shows the status of the stapling operation. The sensors that are used to provide this visual information can also be employed to prevent accidental release of the staples.

Figure 15A:
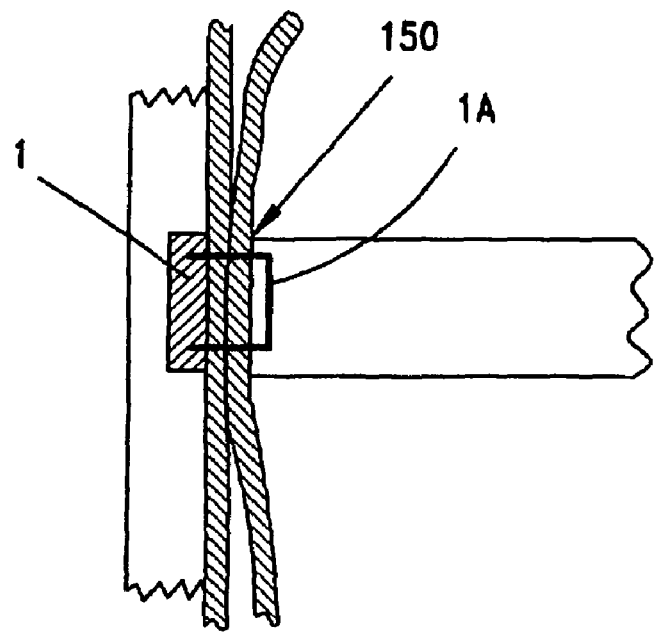
FIG. 15A schematically illustrates the stapling procedure showing the locking needles deployed from the anvil and locked into the staple cartridge.

FIG. 15A illustrates the situation at this stage of the surgical operation. The locking pins (collectively indicated at 150), that were stored in the anvil assembly 1A, have been deployed through the tissue of the fundus and esophagus walls, and have been locked into the sockets in the stapler cartridge 1. The locking pins not only assure proper alignment, but also maintain the desired tissue gap during the stapling. The locking pins (or similar or equivalent locking means) are the reason that the stapler of this invention can function with a totally flexible connection between it's two sections as opposed to the rigid or semi-rigid connection between the anvil and staple container/ejector parts of the staplers of the prior art.

To fire an array of staples, a cable attached to the firing plunger (52 in FIG. 5A and FIG. 5B) is then pulled proximally. This pulls back the cross member (73 in FIGS. 7 and 8A to 8D) with the attached cams. The process of firing the staples can be understood from FIGS. 8A to 8D. As the cam (70) moves proximally, its angled surface engages the angled surface of the staple pusher (66) forcing the pusher to move sidewards towards the wall of the cartridge and forcing the staple (63) out of the side of the cartridge through the tissue of the walls of the esophagus and stomach. The legs of the staple engage the depressions on the face of the anvil and start to curl. FIGS. 8A through 8D show various stages in the firing of one array of staples. After all staples of the array are fired, the release cams (71 in FIG. 7) exert force on the proximal end of the pawls to release the latching of the pins. The distal cable that activated clamping is pulled to withdraw the pins into the anvil and this phase of the surgical operation is completed.

Figure 15B:
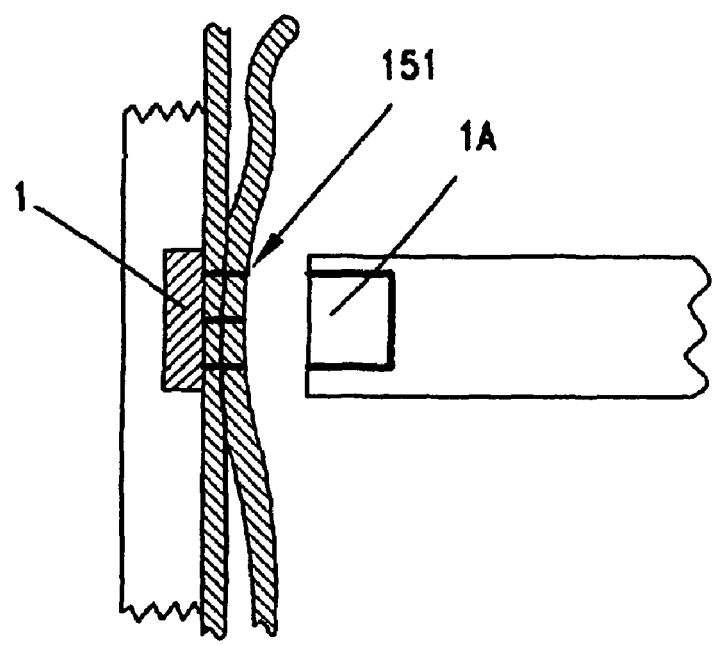
FIG. 15B schematically illustrates the stapling procedure showing the situation after the staples have been fired and the locking needles withdrawn.

FIG. 15B shows the situation after the stapling has been effected. Staples, (collectively indicated at 151), have engaged between the fundus and the esophagus, at the specific location on which it was operated.

The tiny holes in the tissue, that result from the action of the alignment and/or locking pins, are similar to holes produced by hypodermic needles, and seal themselves. The holes can be protected by the staple above and below it. In a preferred embodiment, a configuration consisting of three rows of staples with the pinholes aligned with the middle row (such as that illustrated in FIG. 3B) is chosen to achieve this end.

Figure 14A:
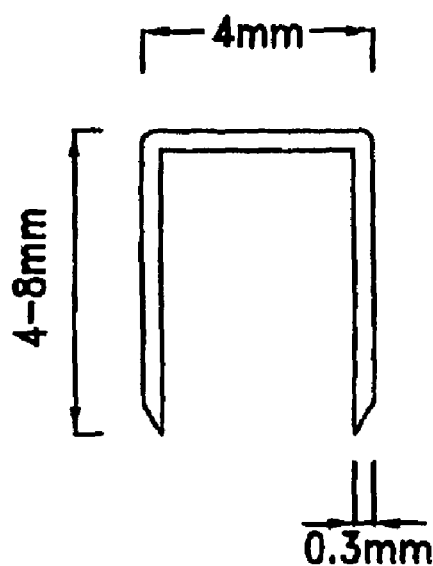
FIG. 14A shows the staple configuration before firing, typical illustrative dimensions being also indicated.
Figure 14B:
FIG. 14B shows the staple configuration after firing.

FIG. 14A shows a staple before firing. FIG. 14B shows the configuration of the staple after the legs are curled in the anvil.

After inspecting the staples the surgeon now releases the articulation section as needed and removes all clamping of tissue inside the stomach. The device is now rotated to the next location and the articulation/aligning procedure is repeated.

The outer two of the three firing cams have spring biased tails that allow the cams to move in one direction only. The firing plunger is now pushed distally and since the cams cannot move in that direction, this causes the whole cartridge to index forward to position the second array opposite the anvil. As the cartridge moves distally, the angled portions on the housing slide out of the first set of windows on the side of the cartridge. Indexing is completed when said portions snap into the second set of windows.

The process of final alignment, deploying and locking the location/locking pins, and firing the second array of staples is repeated. In the case of the embodiment containing three arrays, the whole process as described above is repeated a third time to complete the partial fundoplication. The number of arrays and/or firings depends on medical considerations that are in turn dependent upon factors such as the medical procedure to be carried out and characteristics of the patient.

In a preferred embodiment of the invention, the alignment and/or locking pins and/or the locking pawls are made of a suitable material such as stainless steel as a safety measure. This material is strong enough to allow the parts to function as described in normal operation, but the pin tips can be broken by the force exerted by unbending the articulating section in the event that the release cams fail to unlock the pins.

After many repeated operations of the endoscope, it is possible that wear of the parts, especially in the articulation section, will lead to difficulty in properly aligning the anvil on the distal tip with the stapler cartridge in the endoscope shaft. This difficulty can be overcome by displacing said portion of the stapling assembly along the axis of the endoscopic device by various means. According to a preferred embodiment of the invention this is achieved by the action of a flexible threaded cable coupled with a female thread located in said portion of the stapling assembly. In one preferred embodiment of the invention the flexible threaded cable is located within the endoscopic device, and is in contact with the female thread through a slit provided in the wall of the body of the endoscopic device. In another alternative preferred embodiment of the invention the flexible threaded cable is embedded in the external wall of the endoscopic device, and is in direct contact with the female thread of the portion of the stapling assembly.

In one preferred form of the invention the flexible threaded cable is rotated using a micrometric assembly, thereby to displace the portion of the stapling assembly positioned within the esophagus by a controlled distance.

In another preferred embodiment of the invention, the alignment and/or locking pins of the hereinabove described embodiments are replaced by screws. The changes in the anvil unit that this necessitates are described with reference to FIGS. 16, 17, 18A, 18B, and 18C.

Figure 16:
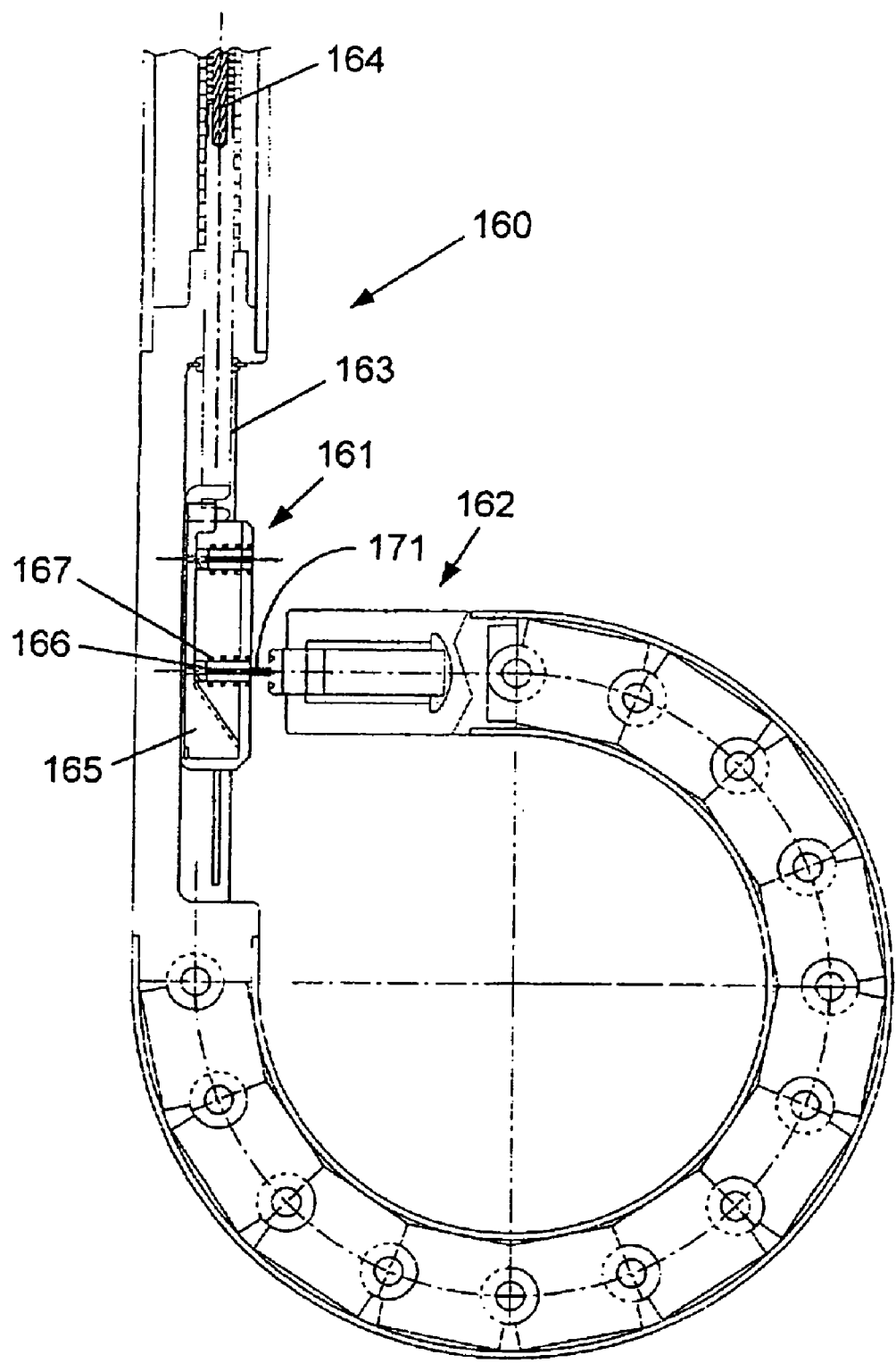
FIG. 16 is a schematic cross-sectional view showing the fixed portion and the articulation distal portion of an endoscope, comprising a stapler consisting of an anvil portion and a staple ejecting portion containing two arrays of staples.

FIG. 16 is a schematic cross-sectional view of the distal section of the endoscope 160 showing the anvil section 162 and the stapler cartridge 161 of the stapler. Parts of the stapler cartridge shown are: one of the firing cams 165, a staple 167, and the corresponding staple pusher 166. The screw 171 is screwed out of the anvil and into the cartridge in order to enable the stapling to be carried out. Numeral 164 designates the firing cable that is attached to plunger 163 that is in turn connected to the cams in the staple cartridge.

Figure 17:
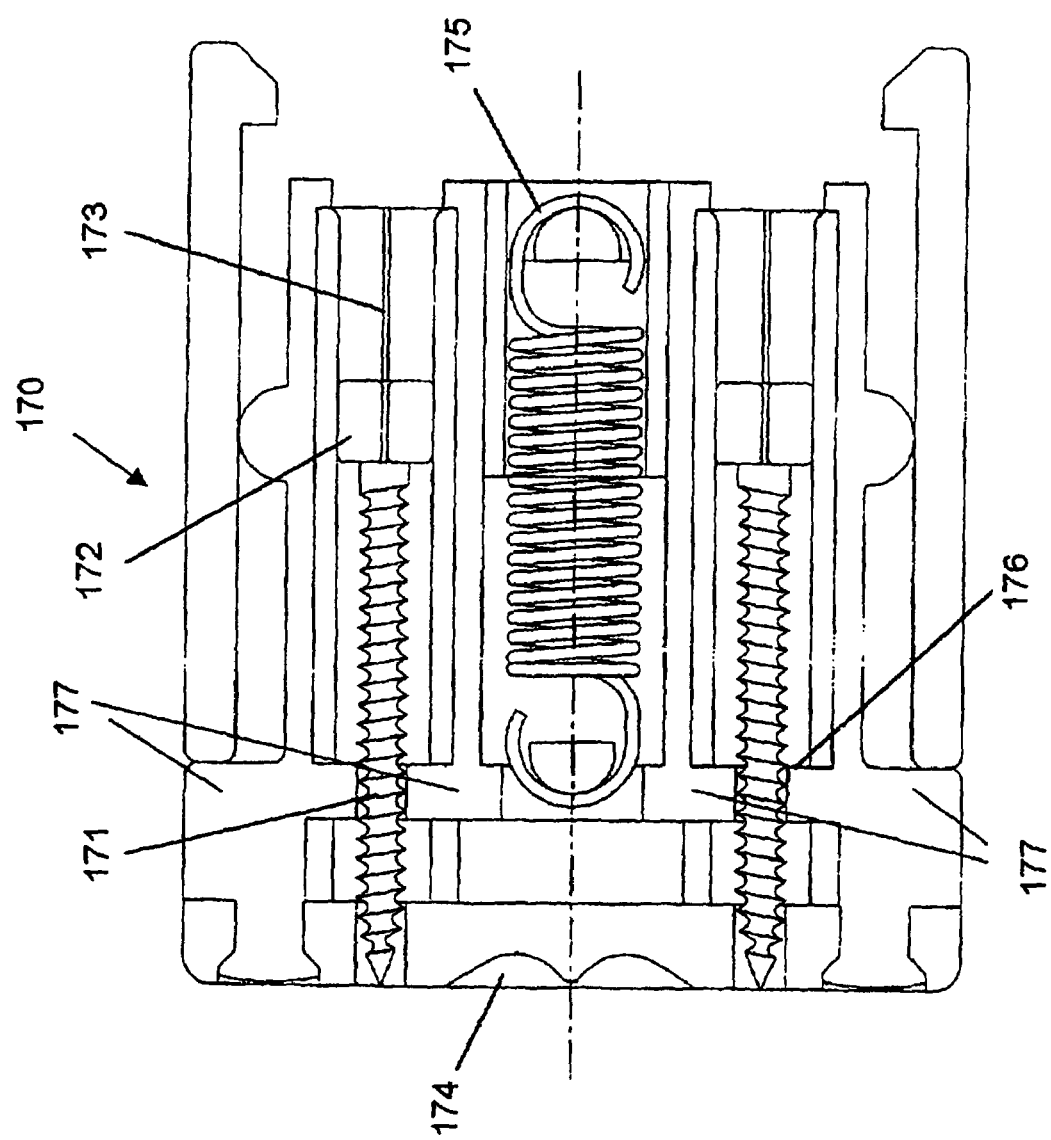
FIG. 17 is a cross-sectional view of an anvil unit, showing the principal components of the replaceable part of the anvil unit, according to another preferred embodiment of the invention.

FIG. 17 is a cross-sectional view showing the principal components of the replaceable part of the anvil unit, generally indicated by numeral 170. The screws 171 have square heads 172. Numeral 173 indicates a tube whose function is to transfer the rotary motion of a set of gears to the heads of the screws, thus causing the screws to rotate and advance out of the anvil. Tubes 173 are round on the outside and square on the inside. When the heads of the screws bottom on surfaces 176, continued rotation pulls parts 177 with the anvil out of the distal end of the endoscope towards the cartridge. Numeral 174 designates the depressions on the face of the anvil that cause the curling of the staples. The spring 175 pulls the anvil back into the distal end of the endoscope when the screws are retracted after disconnecting the anvil from the cartridge.

Figure 18A:
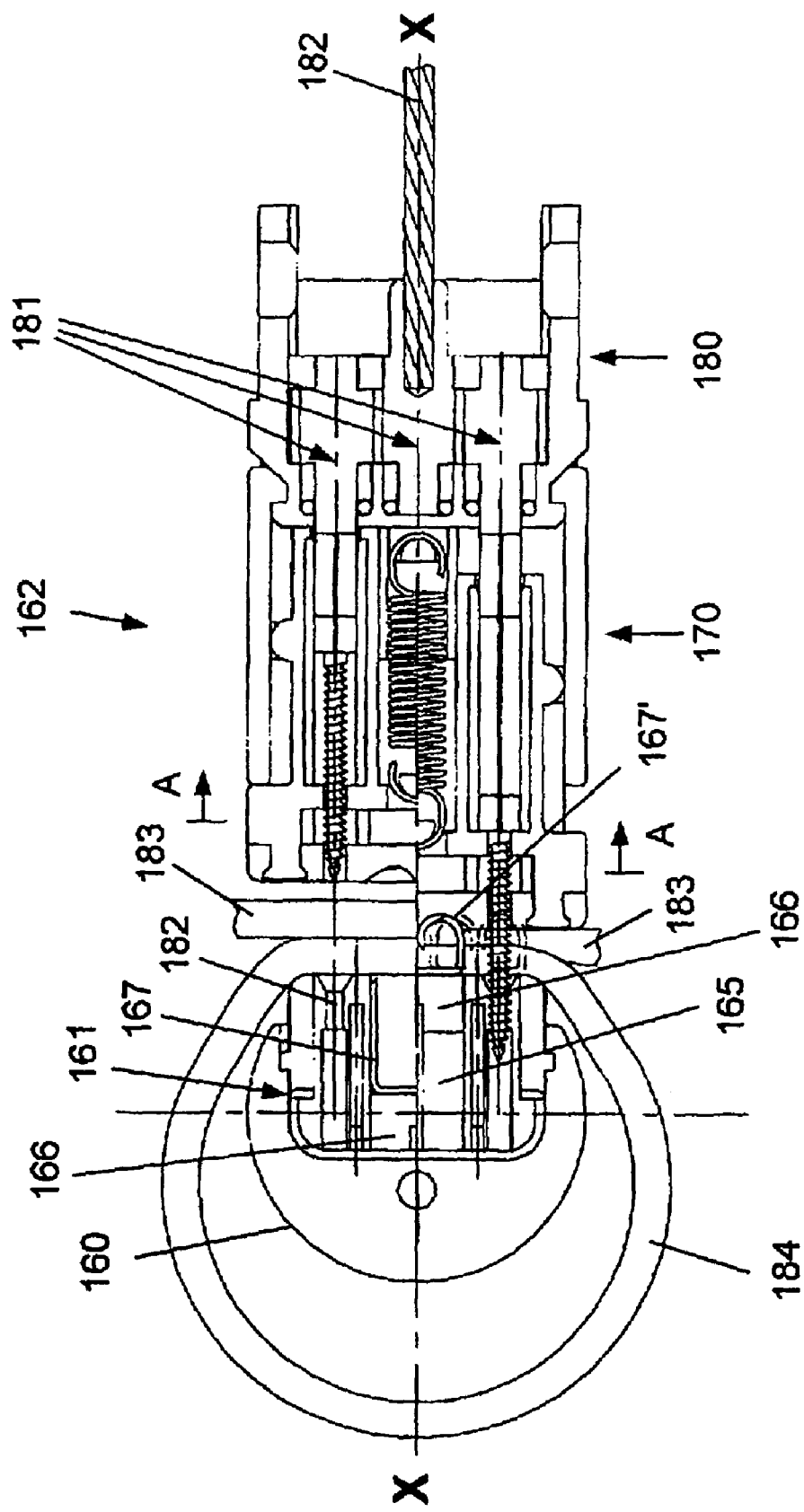
FIG. 18A is a schematic cross-sectional view showing the principal features of the cartridge and anvil sections of the stapler according to a preferred embodiment of the invention.
Figure 18B:
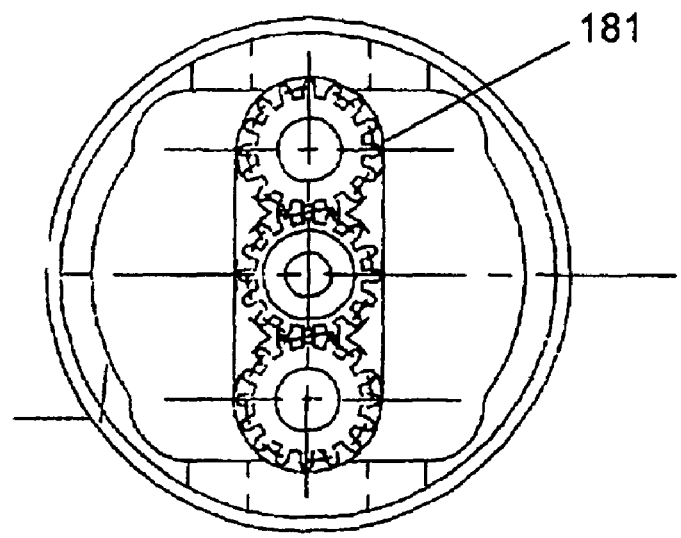
FIG. 18B illustrates the arrangement of gears used to rotate the screws in a preferred embodiment of the invention.

FIG. 18A is a schematic cross-sectional view of the anvil unit and of the cartridge, in the plane orthogonal to that of FIG. 16. FIG. 18A shows the principal features of the cartridge 161 and anvil sections 162 needed to describe the operation of the stapler. The top half of FIG. 18A (above line X-X) shows the situation before the screws are advanced and the bottom half of the figure (below line X-X) shows the anvil connected to the stapler after the staples have been fired. Numeral 160 designates the endoscope and 183 and 184 two layers of tissue that are to be stapled together. In the case of the GERD operation, for example, 183 is the tissue of the fundus and 184 of the esophagus.

The anvil section 162 is composed of two parts: the replaceable unit 170, described with reference to FIG. 17, and parts, generally designated by 180, that are permanently mounted in the distal tip of the endoscope. Part 180 contains three gears 181 whose positions are shown by arrows in FIG. 18A and which are shown in detail FIG. 18B, which is an end view of the distal tip looking in the direction of the staple cartridge. The middle gear is connected to a screw drive cable 182 that extends throughout the length of the endoscope and is rotated at the proximal end. The cable and means of operating it are well known in the art and will not be further described here. The two side gears are each attached to one of the tubes 173. Thus rotation of the screw drive cable causes rotation of the gears which causes the screws to advance or retract.

Figure 18C:
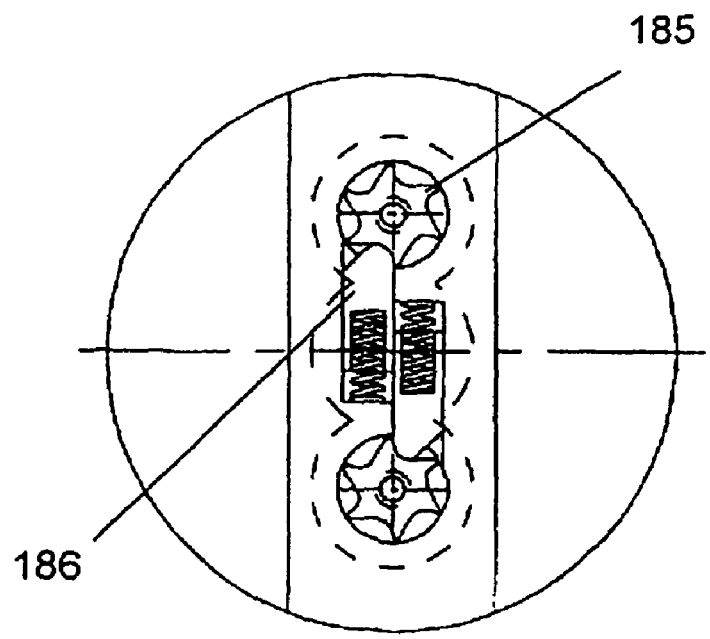
FIG. 18C illustrates the clutch assembly that allows the screws to advance and be retracted in a preferred embodiment of the invention.

FIG. 18C shows a cross-section taken along the A-A plane of the anvil unit. Numeral 185 indicates nuts, through which screws 171 pass, and numeral 186 a clutch system. The system shown in FIG. 18C initially pilots the screw through the tissue and into the staple cartridge. The nuts 185 have an outside sawtooth configuration. Thus, as rotation continues, they allow clamping. When retracting the screws, the nuts cannot rotate. Therefore positive screw withdrawal is achieved.

The cartridge 161 contains several arrays of staples 167, staple pushers 166, and firing cams 165 the operation of which has been described hereinabove. Each array of staples is accompanied by two holes 182 into which the screws in the anvil section enter. The inside of the holes can be threaded; but, in a preferred embodiment of the invention, the cartridge is made of plastic and the screws 171 are self tapping screws that create their own threads as they are advanced into the cartridge. The cartridge described for the embodiments of the invention that use alignment and/or locking pins can also be used with this embodiment, however, since the pawls and springs shown in FIG. 6B as well as the two outside cams shown in FIG. 7 are unnecessary in the case of screws, a much simpler to produce cartridge that doesn't include these parts is preferred.

The sequence of operations that is followed in the use of this embodiment of the invention will now be briefly described. The endoscope is inserted into the patient and the articulation portion is now curled through 270°. Using ultrasonic techniques, as described in the above referenced International Patent Application PCT/IL01/00238, or by any other suitable technique, the relative alignment of the cartridge and anvil are determined. If necessary, the alignment can be adjusted by pushing the staple firing cable to index the cartridge a little past the theoretical alignment point and then, guided by the ultrasonics or other means, retracting the firing cable until exact alignment is achieved. Alternatively, if the original position is short of alignment, the fringing cable is pushed further, using conventional fine controls on the cable, to achieve final alignment. The situation at this stage in the operation is depicted in the upper half of FIG. 18A (above the X-X line).

The screw drive cable is now rotated and, through the gearing, the screws advance through the tissue and into the cartridge. Continued rotation pulls ("telescopes") the anvil from the distal end of the endoscope clamping the tissue. The distance between the anvil and cartridge is measured, for instance, by using the ultrasound system, as described in PCT/IL01/00238, or by any other suitable means, and, if no further adjustments are necessary, the staple firing cable is pulled. Pulling the staple firing cable draws back the cams in the cartridge firing the first array of staples. The situation at this stage of the operation is depicted in the lower half of FIG. 18A (below the X-X line), wherein 167' shows a staple ejected from the cartridge through the layers of tissue and whose legs have been curled by being forced into the depressions on the face of the anvil.

The screw drive cable is now rotated in the opposite direction. This withdraws the screws from the cartridge and tissue and the anvil retracts back into the distal end of the endoscope. The articulation section is now straightened out and the staple cartridge indexed to the next position and the second array of staples is now ready to be deployed if so desired. While embodiments of the invention have been described by way of illustration, it will be understood that the invention can be carried out by persons skilled in the art with many modifications, variations and adaptations, without departing from its spirit or exceeding the scope of the claims.

The invention claimed is:

1. A method of performing a fundoplication of a fundus of a stomach, comprising the steps of:
    (i) inserting an elongated apparatus comprising only one proximal longitudinal portion, only one distal portion, and a surgical fastener ejector transorally through the esophagus into the stomach;
    (ii) contacting a first portion of the fundus with said distal portion of said apparatus without clamping the gastroesophageal junction to urge only the first portion of the fundus toward the proximal longitudinal portion of said elongated apparatus of step (i), wherein the step of contacting the first portion of the fundus comprises bending said distal portion by a fixed radius; and
    (iii) inserting at least one surgical fastener into said first portion of the fundus, wherein said apparatus is in contact with only one portion of said stomach when said at least one surgical fastener is inserted.

2. The method of claim 1, wherein the step of contacting the first portion of the fundus comprises pressing the distal portion of the elongated apparatus against the first portion of the fundus to restrain the first portion of the fundus against movement during the step of inserting the at least one surgical fastener.

3. The method of claim 2, further comprising the steps of:
    (i) moving the distal portion to release the first portion of the fundus from restraint by the distal portion;
    (ii) rotating the distal portion about a longitudinal axis of the elongated apparatus;
    (iii) contacting the distal portion against a second portion of the fundus to urge the second portion of the fundus toward the proximal longitudinal portion; and
    (iv) inserting at least one surgical fastener into the second portion of the fundus.

4. The method of claim 1, wherein the step of inserting at least one surgical fastener comprises inserting an array of surgical fasteners.

5. The method of claim 1, wherein the at least one surgical fastener is a surgical staple(s).

6. The method of claim 3, wherein the at least one surgical fastener is a surgical staple(s).

7. The method of claim 4, wherein the at least one surgical fastener is a surgical staple(s).

8. The method of claim 1, wherein the elongated apparatus is an endoscopic device.

9. The method of claim 2, wherein the proximal longitudinal portion includes a surgical fastener ejector, the distal portion defines at least one void and the step of inserting the at least one surgical fastener comprises ejecting at least a portion of the at least one surgical fastener from the surgical fastener ejector toward the at least one void.

10. The method of claim 2, further comprising the step of holding the longitudinal portion and the distal portion at a fixed separation distance during the step of inserting the at least one surgical fastener.

11. The method of claim 9, wherein the distal portion has a thickness and a depth of the at least one void is less than the thickness of the distal portion, the at least one surgical fastener is at least one surgical staple and the step of ejecting at least a portion of the at least one surgical fastener from the surgical fastener ejector toward the at least one void further comprises striking the bottom of the at least one void with a leg of the at least one surgical fastener with sufficient force to bend the leg.

\* \* \* \* \*